(12) United States Patent
Yang et al.

(10) Patent No.: US 6,455,683 B1
(45) Date of Patent: Sep. 24, 2002

(54) DNA MOLECULES ENCODING HUMAN CLAX PROTEINS AND THEIR SOLUBLE FUSION PROTEINS

(75) Inventors: Guchen Yang, Morrisville, PA (US); Xiaorong Chen, Princeton, NJ (US); Patricia M. Davis, Yardley; Peter A. Kiener, Doylestown, both of PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/531,056

(22) Filed: Mar. 20, 2000

Related U.S. Application Data

(60) Provisional application No. 60/126,149, filed on Mar. 25, 1999.

(51) Int. Cl.$^7$ .............................................. C07H 21/02
(52) U.S. Cl. ................... 536/23.1; 536/23.1; 435/69.1; 435/320.1; 530/350; 530/300
(58) Field of Search .................. 530/300, 350; 435/69.1, 320.1; 536/23.1

(56) References Cited

FOREIGN PATENT DOCUMENTS

| WO | WO 97/40069 | * 10/1997 |
| WO | WO97/40151 | 10/1997 |
| WO | WO 97/40151 | * 10/1997 |

OTHER PUBLICATIONS

L. Lanier, Annu. Rev. Immunol., 1998, 16, 359–393.
R. Testi et al., Immunol. Today, 1994, 15, 479–483.
M. Lopez–Cabrera et al., J. Exp. Med., 1993, 178, 537–547.
M. C. Nakamura et al., J. Exp. Med., 1997, 185, 4, 673–684.
F. Vely et al., J. Immunol., 1997, 159, 2075–2077.
K. M. Smith et al., J. Immunol, 1998, 161, 7–10.
N. Kashima et al., Nature, 1985, 313, 402–404.
S. Needleman et al., J. Mol. Biol., 1970, 48, 443–453.
L. Lanier et al., Immunity, 1998, 8, 693–701.
J. Ryan et al., Immunol. Rev., 1997, 155, 79–89.
J. Hamann et al., Ummunogenetics, 1997, 45, 295–300.
Devereux et al., Nucl. Acids Res., 1984, 12, 1, 387–395.
Smith et al., Adv. Appl. Math1981, 2, 482–489.

* cited by examiner

*Primary Examiner*—Karen Cochrane Carlson
*Assistant Examiner*—Hope A. Robinson
(74) *Attorney, Agent, or Firm*—Audrey F. Sher

(57) ABSTRACT

Isolated novel cDNA sequences encoding a human C-type lectin and three homologues are provided. They are referred to herein as "CLAX" (C-type Lectin, Activation Expressed) proteins. The invention also includes methods of using the nucleic acid sequences, polypeptides encoded by the nucleic acid sequences disclosed herein, fusion proteins having all or a portion (e.g., an extracellular region) of the CLAX proteins, antibodies specific for the novel CLAXs, ligands and inhibitors for the novel CLAXs. The genes of CLAX are specifically expressed in lymphoid tissues and activated T lymphocytes but not resting T lymphocytes. The invention concerns the utility in pharmaceutical compositions for the prevention and treatment of infectious, inflammatory and allergic diseases.

13 Claims, 10 Drawing Sheets

Human CLAX

```
GCAAA ATG CAT GAC AGT AAC AAT GTG GAG AAA GAC ATT ACA      41
      M   H   D   S   N   N   V   E   K   D   I   T

CCA TCT GAA TTG CCT GCA AAC CCA GGT TGT CTG CAT TCA AAA     83
 P   S   E   L   P   A   N   P   G   C   L   H   S   K

GAG CAT TCT ATT AAA GCT ACC TTA ATT TGG CGC TTA TTT TTC    125
 E   H   S   I   K   A   T   L   I   W   R   L   F   F

TTA ATC ATG TTT CTG ACA ATC ATA GTG TGT GGA ATG GTT GCT    167
 L   I   M   F   L   T   I   I   V   C   G   M   V   A

GCT TTA AGC GCA ATA AGA GCT AAC TGC CAT CAA GAG CCA TCA    209
 A   L   S   A   I   R   A   N   C   H   Q   E   P   S

GTA TGT CTT CAA GCT GCA TGC CCA GAA AGC TGG ATT GGT TTT    251
 V   C   L   Q   A   A   C   P   E   S   W   I   G   F

CAA AGA AAG TGT TTC TAT TTT TCT GAT GAC ACC AAG AAC TGG    293
 Q   R   K   C   F   Y   F   S   D   D   T   K   N   W

ACA TCA AGT CAG AGG TTT TGT GAC TCA CAA GAT GCT GAT CTT    335
 T   S   S   Q   R   F   C   D   S   Q   D   A   D   L

GCT CAG GTT GAA AGC TTC CAG GAA CTG AAT TTC CTG TTG AGA    377
 A   Q   V   E   S   F   Q   E   L   N   F   L   L   R

TAT AAA GGC CCA TCT GAT CAC TGG ATT GGG CTG AGC AGA GAA    419
 Y   K   G   P   S   D   H   W   I   G   L   S   R   E

CAA GGC CAA CCA TGG AAA TGG ATA AAT GGT ACT GAA TGG ACA    461
 Q   G   Q   P   W   K   W   I   N   G   T   E   W   T

AGA CAG TTA GTC ATG AAA GAA GAT GGT GCC AAC TTG TAT GTT    503
 R   Q   L   V   M   K   E   D   G   A   N   L   Y   V

GCA AAG GTT TCA CAA GTT CCT CGA ATG AAT CCA AGA CCT GTC    545
 A   K   V   S   Q   V   P   R   M   N   P   R   P   V

ATG GTT TCC TAT CCT GGG AGC AGG AGA GTG TGC CTA TTT GAA    587
 M   V   S   Y   P   G   S   R   R   V   C   L   F   E

TGA CAAAGGTGCC AGTAGTGCCA GGCACTACAC AGAGAGGAAG            630
 *

TGGATTTGTT  CCAAATCAGA  TATACATGTC  TAGATGTTAC  AGCAAAGCCC  680
CAACTAATCT  TTAGAAGCAT  ATTGGAACTG  ATAACTCCAT  TTTAAAATGA  730
GCAAAGAATT  TATTTCTTAT  ACCAACAGGT  ATATGAAAAT  ATGCTCAATA  780
TCACTAATAA  CTGGGAAAAT  ACAATCAAAA  TCATAGTAAA  ATATTACCTG  830
TTTTCATGGT  GCTAATATTA  CCTGTTCTCC  CACTGCTAAT  GACATACCCG  880
AGACTGAGTA  ATTTATAAAT  AAAAGAGATT  TAATTGAAAA  AAAAAAAAA   930
A                                                          931
```

FIG. 2A

CLAX clone7B

| | | | | | | | | | | | | | |
|---|---|---|---|---|---|---|---|---|---|---|---|---|---|
| TGT | CTG | CAT | TCA | AAA | GAG | CAT | TCT | ATT | AAA | GCT | ACC | TTA | ATT | 42 |
| C | L | H | S | K | E | H | S | I | K | A | T | L | I | |
| TGG | CGC | TTA | TTT | TTC | TTA | ATC | ATG | TTT | CTG | ACA | ATC | ATA | GTG | 84 |
| W | R | L | F | F | L | I | M | F | L | T | I | I | V | |
| TGT | GGA | ATG | GTT | GCT | GCT | TTA | AGC | GCA | ATA | AGA | GCT | AAC | TGC | 126 |
| C | G | M | V | A | A | L | S | A | I | R | A | N | C | |
| CAT | CAA | GAG | CCA | TCA | GTA | TGT | CTT | CAA | GCT | GCA | TGC | CCA | GAA | 168 |
| H | Q | E | P | S | V | C | L | Q | A | A | C | P | E | |
| AGC | TGG | ATT | GGT | TTT | CAA | AGA | AAG | TGT | TTC | TAT | TTT | TCT | GAT | 210 |
| S | W | I | G | F | Q | R | K | C | F | Y | F | S | D | |
| GAC | ACC | AAG | AAC | TGG | ACA | TCA | AGT | CAG | AGG | TTT | TGT | GAC | TCA | 252 |
| D | T | K | N | W | T | S | S | Q | R | F | C | D | S | |
| CAA | GAT | GCT | GAT | CTT | GCT | CAG | GTT | GAA | AGC | TTC | CAG | GAA | CTG | 294 |
| Q | D | A | D | L | A | Q | V | E | S | F | Q | E | L | |
| AAT | TTC | CTG | TTG | AGA | TAT | AAA | GGC | CCA | TCT | GAT | CAC | TGG | ATT | 336 |
| N | F | L | L | R | Y | K | G | P | S | D | H | W | I | |
| GGG | CTG | AGC | AGA | GAA | CAA | GGC | CAA | CCA | TGG | AAA | TGG | ATA | AAT | 378 |
| G | L | S | R | E | Q | G | Q | P | W | K | W | I | N | |
| GGT | ACT | GAA | TGG | ACA | AGA | CAG | TTA | GTC | ATG | AAA | GAA | GAT | GGT | 420 |
| G | T | E | W | T | R | Q | L | V | M | K | E | D | G | |
| GCC | AAC | TTG | TAT | GTT | GCA | AAG | GTT | TCA | CAA | GTT | CCT | CGA | ATG | 462 |
| A | N | L | Y | V | A | K | V | S | Q | V | P | R | M | |
| AAT | CCA | AGA | CCT | GTC | ATG | GTT | TCC | TAT | CCT | GGG | AGC | AGG | AGA | 504 |
| N | P | R | P | V | M | V | S | Y | P | G | S | R | R | |
| GTG | TGC | CTA | TTT | GAA | TGA | CAA | AGG | TGC | CAG | TAG | TGC | CAG | GCA | 546 |
| V | C | L | F | E | * | Q | R | C | Q | * | C | Q | A | |
| CTA | CAC | AGA | GAG | GAA | GTG | GAT | TTG | TTC | CAA | ATC | AGA | TAT | ACA | 588 |
| L | H | R | E | E | V | D | L | F | Q | I | R | Y | T | |
| TGT | CTA | GAT | GTT | ACA | GCA | AAG | CCC | CAA | CTA | ATC | TTT | AGA | AGC | 630 |
| C | L | D | V | T | A | K | P | Q | L | I | F | R | S | |
| ATA | TTG | GAA | CTG | ATA | ACT | CCA | TTT | TAA | AAT | GAG | CAA | AGA | ATT | 672 |
| I | L | E | L | I | T | P | F | * | N | E | Q | R | I | |
| TAT | TTC | TTA | TAC | CAA | CAG | GTA | TAT | GAA | AAT | ATG | CTC | AAT | ATC | 714 |
| Y | F | L | Y | Q | Q | V | Y | E | N | M | L | N | I | |

FIG. 2B-1

```
ACT AAT AAC TGG GAA AAT ACA AAT CAA AAT CAT AGT AAA ATA  756
 T   N   N   W   E   N   T   N   Q   N   H   S   K   I

TTA CCT GTT TTC ATG GTG CTA ATA TTA CCT GTT CTC CCA CTG  798
 L   P   V   F   M   V   L   I   L   P   V   L   P   L

CTA ATG ACA TAC CCG AGA CTG AGT AAT TTA TAA ATA AAA GAG  840
 L   M   T   Y   P   R   L   S   N   L   *   I   K   E

ATT TAA TTG AAA AAA AAA AAA AAA                          864
 I   *   L   K   K   K   K   K
```

FIG. 2B-2

CLAX clone 2I

```
GC AAA ATG CAT GAC AGT AAC AAT GTG GAG AAA GAC ATT ACA  41
   K   M   H   D   S   N   N   V   E   K   D   I   T

CCA TCT GAA TTG CCT GCA AAC CCA GGT TGT CTG CAT TCA AAA  83
 P   S   E   L   P   A   N   P   G   C   L   H   S   K

GAG CAT TCT ATT AAA GCT ACC TTA ATT TGG CGC TTA TTT TTC 125
 E   H   S   I   K   A   T   L   I   W   R   L   F   F

TTA ATC ATG TTT CTG ACA ATC ATA GTG TGT GGA ATG GTT GCT 167
 L   I   M   F   L   T   I   I   V   C   G   M   V   A

GCT TTA AGC GCA ATA AGA GCT AAC TGC CAT CAA GAG CCA TCA 209
 A   L   S   A   I   R   A   N   C   H   Q   E   P   S

GTA TGT CTT CAA GCT GCA TGC CCA GAA AGC TGG ATT GGT TTT 251
 V   C   L   Q   A   A   C   P   E   S   W   I   G   F

CAA AGA AAG TGT TTC TAT TTT TCT GAT GAC ACC AAG AAC TGG 293
 Q   R   K   C   F   Y   F   S   D   D   T   K   N   W

ACA TCA AGT CAG AGG TTT TGT GAC TCA CAA GAT GCT GAT CTT 335
 T   S   S   Q   R   F   C   D   S   Q   D   A   D   L

GCT CAG GTT GAA AGC TTC CAG GAA CTG AAT TTC CTG TTG AGA 377
 A   Q   V   E   S   F   Q   E   L   N   F   L   L   R

TAT AAA GGC CCA TCT GAT CAC TGG ATT GGG CTG AGC AGA GAA 419
 Y   K   G   P   S   D   H   W   I   G   L   S   R   E

CAA GGC CAA CCA TGG AAA TGG ATA AAT GGT ACT GAA TGG ACA 461
 Q   G   Q   P   W   K   W   I   N   G   T   E   W   T

AGA CAG TTT CCT ATC CTG GGA GCA GGA GAG TGT GCC TAT TTG 503
 R   Q   F   P   I   L   G   A   G   E   C   A   Y   L

AAT GAC AAA GGT GCC AGT AGT GCC AGG CAC TAC ACA GAG AGG 545
 N   D   K   G   A   S   S   A   R   H   Y   T   E   R

AAG TGG ATT TGT TCC AAA TCA GAT ATA CAT GTC TAG ATG TTA 587
 K   W   I   C   S   K   S   D   I   H   V   *   M   L

CAG CAA AGC CCC AAC TAA TCT TTA GAA GCA TAT TGG AAC TGA 629
 Q   Q   S   P   N   *   S   L   E   A   Y   W   N   *

TAA CTC CAT TTT AAA ATG AGC AAA GAA TTT ATT TCT TAT ACC 671
 *   L   H   F   K   M   S   K   E   F   I   S   Y   T

AAC AGG TAT ATG AAA ATA TGC TCA ATA TCA CTA ATA ACT GGG 713
 N   R   Y   M   K   I   C   S   I   S   L   I   T   G
```

FIG. 2C-1

```
AAA ATA CAA ATC AAA ATC ATA GTA AAA TAT TAC CTG TTT TCA 755
 K   I   Q   I   K   I   I   V   K   Y   Y   L   F   S

TGG GGC TAA TAT TAC CTG TTC TCC CAC TGC TAA TGA CAT ACC 797
 W   G   *   Y   Y   L   F   S   H   C   *   *   H   T

CGA GAC TGA GTA ATT TAT AAA TAA AA                      823
 R   D   *   V   I   Y   K   *
```

FIG. 2C-2

CLAX clone4A

```
GAG CAT TCT ATT AAA GCT ACC TTA ATT TGG CGC TTA TTT TTC  42
 E   H   S   I   K   A   T   L   I   W   R   L   F   F

TTA ATC ATG TTT CTG ACA ATC ATA GTG TGT GGA ATG GTT GCT  84
 L   I   M   F   L   T   I   I   V   C   G   M   V   A

GCT TTA AGC GCA ATA AGA GCT AAC TGC CAT CAA GAG CCA TCA 126
 A   L   S   A   I   R   A   N   C   H   Q   E   P   S

GTA TGT CTT CAA GCT GCA TGC CCA GAA AGC TGG ATT GGT TTT 168
 V   C   L   Q   A   A   C   P   E   S   W   I   G   F

CAA AGA AAG TGT TTC TAT TTT TCT GAT GAC ACC AAG AAC TGG 210
 Q   R   K   C   F   Y   F   S   D   D   T   K   N   W

ACA TCA AGT CAG AGG TTT TGT GAC TCA CAA GAT GCT GAT CTT 252
 T   S   S   Q   R   F   C   D   S   Q   D   A   D   L

GCT CAG GTT GAA AGC TTC CAG GAA CTG GTT TCC TAT CCT GGG 294
 A   Q   V   E   S   F   Q   E   L   V   S   Y   P   G

AGC AGG AGA GTG TGC CTA TTT GAA TGA CAA AGG TGC CAG TAG 336
 S   R   R   V   C   L   F   E   *   Q   R   C   Q   *

TGC CAG GCA CTA CAC AGA GAG GAA GTG GAT TTG TTC CAA ATC 378
 C   Q   A   L   H   R   E   E   V   D   L   F   Q   I

AGA TAT ACA TG                                           389
 R   Y   T
```

FIG. 2D

Human CLAX (7B) AND ITS VARIANTS (2I, AND 4A)

```
7B                                    CLHSKEHS   IKATLIWRLF  FLIMFLTIIV
2I    MHDSNNVEK  DITPSELPAN  PGCLHSKEHS   IKATLIWRLF  FLIMFLTIIV
4A                                    EHS   IKATLIWRLF  FLIMFLTIIV

7B    CGMVAALSAI  RANCHQEPSV  CLQAACPESW  IGFQRKCFYF  SDDTKNWTSS
2I    CGMVAALSAI  RANCHQEPSV  CLQAACPESW  IGFQRKCFYF  SDDTKNWTSS
4A    CGMVAALSAI  RANCHQEPSV  CLQAACPESW  IGFQRKCFYF  SDDTKNWTSS

7B    QRFCDSQDAD  LAQVESFQEL  NFLLRYKGPS  DHWIGLSREQ  GQPWKWINGT
2I    QRFCDSQDAD  LAQVESFQEL  NFLLRYKGPS  DHWIGLSREQ  GQPWKWINGT
4A    QRFCDSQDAD  LAQVESFQEL  VSYPGSRRVC  LFE*

7B    EWTRQLVMKE  DGANLYVAKV  SQVPRMNPRP  VMVSYPGSRR  VCLFE*
2I    EWTRQFPILG  AGECAYLNDK  GASSARHYTE  RKWICSKSDI  HV*
4A
```

FIG. 3A

Amino acid sequence alignment of the C-type lectin family

```
hCLAX-7B   73   AACPESWIG  FQRKCFYFSD  DTKNWTSSQR  FCDSQDADLA
hCLAX-2I   73   AACPESWIG  FQRKCFYFSD  DTKNWTSSQR  FCDSQDADLA
hCLAX-4A   73   AACPESWIG  FQRKCFYFSD  DTKNWTSSQR  FCDSQDADLA hCD69      83   SSCSEDWVG  YQRKCYFIST  VKRSWTSAQN  ACSEHGATLA
chk17.5   584   HVCPNAWVG  FQGKCYYFSD  TESDWNSSRE  HCHRLGASLA
hAICL      33   SLCPYDWIG  FQNKCYYFSK  EEGDWNSSKY  NCSTQHADLT
hASGPR    156   TCCPVNWVE  HQGSCYWFSH  SGKAWAEAEK  YCQLENAHLV
hCD94      59   CSCQEKWVG  YRCNCYFISS  EQKTWNESRH  LCASQKSSLL
hMAFA      73   PSCPDRWMK  YGNHCYYFSV  EEKDWNSSLE  FCLARDSHLL
hCD23     161   NTCPEKWIN  FQRKCYYFGK  GTKQWVHARY  ACDDMEGQLV
                    *    *         *          *         *     *

QVESFQELNF  LLRYKGPSDH  WIGLSREQGQ  P.WKWINGTE  150
           QVESFQELNF  LLRYKGPSDH  WIGLSREQGQ  P.WKWINGTE  150
           QVESFQEL                                        119

VIDSEKDMNF  LKRYAGREEH  WVGLKKEPGH  P.WKWSNGKE  160
           TLDTKEEMEF  MLQYQRPADR  WIGLHRAEGD  EHWTWADGSA  663
           IIDNIEEMNF  LRRYKCSSDH  WIGLKMAKNR  T.GQWVHGAT  110
           VINSWEEQKF  IVQHTNPFNT  WIGLTDSD..  GSWKVVDGTD  232
           QLQNTDELDF  MS..SSQQFY  WIGLSYSEEH  TAWLWENGSA  135
           VITDNQEMSL  LQVFLSEAFC  WIGL...RNN  SGWRWEDGSP  148
           SIHSPEEQDF  LTKHASHTGS  WIGLRNLDLK  GEFIWVDGSH  239
                *  **          *  **                *  *
```

FIG. 3B

FUSION PROTEINS OF HUMAN CLAX (18) AND ITS VARIANTS (5, AND 13)

```
18   MASPLTRFLS  LNLLLLGESI  ILGSGEAKPQ  APELRIFPKK  MDAELGQKVD
5    MASPLTRFLS  LNLLLLGESI  ILGSGEAKPQ  APELRIFPKK  MDAELGQKVD
13   MASPLTRFLS  LNLLLLGESI  ILGSGEAKPQ  APELRIFPKK  MDAELGQKVD

18   LVCEVLGSVS  QGCSWLFQNS  SSKLPQPTFV  YMASSHNKIT  WDEKLNSSKL
5    LVCEVLGSVS  QGCSWLFQNS  SSKLPQPTFV  YMASSHNKIT  WDEKLNSSKL
13   LVCEVLGSVS  QGCSWLFQNS  SSKLPQPTFV  YMASSHNKIT  WDEKLNSSKL

18   FSAMRDTNNK  YVLTLNKFSK  ENEGYYFCSV  ISNSVMYFSS  VVPVLQKVNS
5    FSAMRDTNNK  YVLTLNKFSK  ENEGYYFCSV  ISNSVMYFSS  VVPVLQKVNS
13   FSAMRDTNNK  YVLTLNKFSK  ENEGYYFCSV  ISNSVMYFSS  VVPVLQKVNS

18   TTTKPVLRTP  SPVHPTGTSQ  PQRPEDCRPR  GSVKGTGLDF  ACDPDPRANC
5    TTTKPVLRTP  SPVHPTGTSQ  PQRPEDCRPR  GSVKGTGLDF  ACDPDPRANC
13   TTTKPVLRTP  SPVHPTGTSQ  PQRPEDCRPR  GSVKGTGLDF  ACDPDPRANC

18   HQEPSVCLQA  ACPESWIGFQ  RKCFYFSDDT  KNWTSSQRFC  DSQDADLAQV
5    HQEPSVCLQA  ACPESWIGFQ  RKCFYFSDDT  KNWTSSQRFC  DSQDADLAQV
13   HQEPSVCLQA  ACPESWIGFQ  RKCFYFSDDT  KNWTSSQRFC  DSQDADLAQV

18   ESFQELNFLL  RYKGPSDHWI  GLSREQGQPW  KWINGTEWTR  QLVMKEDGAN
5    ESFQELNFLL  RYKGPSDHWI  GLSREQGQPW  KWINGTEWTR  QFPILGAGEC
13   ESFQELVSYP  GSRRVCLFE*

18   LYVAKVSQVP  RMNPRPVMVS  YPGSRRVCLF  E*
5    AYLNDKGASS  ARHYTERKWI  CSKSDIHV*
13
```

FIG. 4

CLAX gene expression in different tissues

Transcription kinetics of CLAX gene during T lymphocyte activation

US 6,455,683 B1

DNA MOLECULES ENCODING HUMAN CLAX PROTEINS AND THEIR SOLUBLE FUSION PROTEINS

CROSS-REFERENCE TO RELATED APPLICATION

This application claims the benefit of U.S. Provisional Application No. 60/126,149 filed Mar. 25, 1999.

FIELD OF THE INVENTION

The invention is generally in the field of infection, inflammation and allergy. More specifically, the present invention concerns three novel DNA molecules encoding three polypeptides, which may be useful in controlling and modulating activation and differentiation of lymphoid cells. The present invention also concerns expression vectors comprising the genes, host cells comprising the expression vectors, proteins produced by the genes, methods for producing the proteins, and methods of using the genes and proteins.

BACKGROUND OF THE INVENTION

Natural killer (NK) cells are lymphocytes that participate in innate immune response against certain bacteria, parasites, and viruses. (Lanier, L. L., (1998) *Annu. Rev. Immunol.* 16:359–393). NK cells express a lectin-like receptor superfamily of type II transmembrane proteins (amino terminus intracellular). Their extracellular domains have structural features of C-type lectins. (Ryan, J. C., et al., (1997) *Immunol. Rev.* 155:79–89). The superfamily consists of several families including Ly-49 (in mice and rats), NKR-P1 (in mice, rats, and humans), NKG2 (in humans and rats), and CD94 (in humans). These proteins are encoded by a single genetic region called the NK gene complex (NKC) which are located on human chromosome 12, mouse chromosome 6 and rat chromosome 4. Different receptors, even within the same family, have been shown to activate or to inhibit NK cell functions. (Vely, F., et al., (1997) *J. Immunol.* 159:2075–2077). In many cases, the different activities mediated by individual receptors have been linked to the different structures of these receptors in their cytoplasmic domain and in their transmembrane domain.

For example, the murine Ly-49D and Ly-49H, and the human NKG2C, which possess a positively charged residue (arginine or lysine) within their transmembrane domain, have been shown to activate NK cells by associating with DAP12 membrane adapter protein. (Smith, K. M., et al., (1998) *J. Immunol.* 161:7–10; Lanier, L. L., et al., (1998) *Immunity* 8:693–701). The DAP12 contains a negatively charged residue (aspartic acid) in its transmembrane region and an immunoreceptor tyrosine-based activating motif (ITAM) in its cytoplasmic domain. Upon cross-linking of CD94/NKG2C, tyrosine residues in ITAM of DAP12 become phosphorylated and recruit tyrosine kinases, such as ZAP-70 or Syk.

On the other hand, the murine Ly-49A that lacks charged residues in its transmembrane region and contains an immunoreceptor tyrosine-based inhibitory motif (ITIM) in its cytoplasmic domain has been demonstrated to inhibit NK cytotoxicity. (Nakamura, M. C., et al., (1997) *J. Exp. Med.* 185:673–684). The inhibitory activity is mediated by cytoplasmic tyrosine phosphatase, SHP-1, which is recruited by the ITIM domain of Ly-49A. The tyrosine phosphatase SHP-1 can dephosphorylate the adjacent adapter proteins and kinases, resulting in the termination of activation signals.

Genes located in NKC also encode other C-type lectins such as CD69 and the recently identified receptor AICL. (Lopez-Cabrera, M., et al., (1993) *J. Exp. Med.* 178:537–547; Hamann, J., et al., (1997) *Immunogenetics* 45:295–300). Unlike the restricted expression of other NK cell receptors, both CD69 and AICL are widely expressed on hematopoietic cells including lymphocytes, monocytes and granulcytes. They are not expressed on resting, but are rapidly induced upon activation. CD69 is known as the earliest activation marker of lymphocytes. Anti-CD69 mAb can induce activation and cytokine production of T, B and NK cells, though CD69 lacks a charged residue in its intracellular domain. (Testi, R., et al., (1994) *Immunol Today.* 15:479–483).

Because of the diverse biological activities of members of the lectin-like receptor superfamily and their close relationship to immune cell functions, those skilled in the art are interested in identifying novel members of this family. The identification and study of novel genes and proteins may lead to a better understanding of the mechanisms underlying immune cell functions, and will permit those skilled in the art to regulate or control immune reactions or diseases.

SUMMARY OF THE INVENTION

The present invention includes a novel "CLAX" protein (C-type Lectin, Activation eXpressed) shown in SEQ ID NO:2 (FIG. 2A) and a nucleic acid sequence (SEQ ID NO:1) encoding said CLAX protein. Additionally encompassed within the invention are nucleic acid sequences encoding homologues to said CLAX protein (FIGS. 2B, 2C and 2D). The homologues are referred to herein as clone 7B (nucleic acid sequence shown in SEQ ID NO:3; amino acid sequence shown in SEQ ID NO:4); clone 2I (nucleic acid sequence shown in SEQ ID NO:5; amino acid sequence shown in SEQ ID NO:6); and clone 4A (nucleic acid sequence shown in SEQ ID NO:7; amino acid sequence shown in SEQ ID NO:8). The nucleotide sequences of the isolated cDNA's are disclosed herein along with the deduced amino acid sequences. The cDNA genes of the above clones have been deposited on Jan. 19, 1999 with the American Type Culture Collection, 10801 University Boulevard, Manassas, Va. 20110–2209 and given the Accession Numbers ATCC 203599 (HuCLAX-7B) (clone 7B); ATCC 203601 (HuCLAX-2I) (clone 2I); and ATCC 203600 (HuCLAX-4A) (clone 4A).

The present inventors sequenced the clones encoding the novel CLAX protein homologues and determined the primary sequences of the deduced proteins. The nucleic acid and amino acid sequences of the novel CLAX protein disclosed herein were determined from the sequenced clones. The novel CLAX protein exhibits sequence identity to the known sequence of human CD69.

The CLAX protein of the present invention can be produced by: (1) inserting the cDNA of a disclosed CLAX into an appropriate expression vector; (2) transfecting the expression vector into an appropriate transfection host(s); (3) growing the transfected host(s) in appropriate culture media; and (4) purifying the protein from the culture media.

The present invention therefore provides a purified and isolated nucleic acid molecule, preferably a DNA molecule, having a sequence which codes for CLAX protein, or an oligonucleotide fragment of the nucleic acid molecule which is unique to a CLAX protein of the present invention. In a preferred embodiment of the invention, the purified and isolated nucleic acid molecule has the sequence as shown in SEQ ID NO:1 (FIG. 2A). In another preferred embodiment, the purified and isolated nucleic acid molecule has the sequence as shown in SEQ ID NO:3 (FIG. 2B). In still another preferred embodiment the purified and isolated nucleic acid molecule has the sequence as shown in SEQ ID NO:5 (FIG. 2C). In still another preferred embodiment of the present invention the purified and isolated nucleic acid molecule has the nucleotide sequence as shown in SEQ ID NO:7 (FIG. 2D).

The invention also contemplates a double stranded nucleic acid molecule comprising a nucleic acid molecule of the invention or an oligonucleotide fragment thereof hydrogen bonded to a complementary nucleotide base sequence.

The terms "isolated and purified nucleic acid" and "substantially pure nucleic acid", e.g., substantially pure DNA, refer to a nucleic acid molecule which is one or both of the following: (1) not immediately contiguous with either one or both of the sequences, e.g., coding sequences, with which it is immediately contiguous (i.e., one at the 5' end and one at the 3' end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure or isolated and purified DNA also includes a recombinant DNA which is part of a hybrid gene encoding additional CLAX sequence.

The present invention provides in one embodiment: (a) an isolated and purified nucleic acid molecule comprising a sequence encoding all or a portion of a protein having the amino acid sequence as shown in SEQ ID NO:2; (b) nucleic acid sequences complementary to (a); (c) nucleic acid sequences which exhibit at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions. In a particular embodiment, the nucleic acid sequence comprises (a) the sequence as shown in SEQ ID NO:1, (b) a nucleic acid sequence complementary to SEQ ID NO:1, and (c) sequences having at least 80%, more preferably at least 90%, more preferably at least 95%, and most preferably at least 98% sequence identity to (a) or (b).

The degree of homology (percent identity) between a native and a mutant sequence may be determined, for example, by comparing the two sequences using computer programs commonly employed for this purpose. One suitable program is the GAP computer program described by Devereux et al., (1984) *Nucl. Acids Res.* 12:387. The GAP program utilizes the alignment method of Needleman and Wunsch (1970) *J. Mol. Biol.* 48:433, as revised by Smith and Waterman (1981) *Adv. Appl. Math.* 2:482. Briefly, the GAP program defines percent identity as the number of aligned symbols (i.e., nucleotides or amino acids) which are identical, divided by the total number of symbols in the shorter of the two sequences.

As used herein the term "stringent conditions" encompasses conditions known in the art under which a nucleotide sequence will hybridize to an isolated and purified nucleic acid molecule comprising a sequence encoding a protein having the amino acid sequence as shown herein, or to (b) a nucleic acid sequence complementary to (a). In a preferred embodiment, stringent conditions comprise overnight incubation at 42° C. in a solution comprising: 50% formamide, 5×SSPE (750 mM NaCl, 50 mM $NaH_2PO_4$ and 5 mM EDTA), 5×Denhardt's solution, 0.1% SDS and 100 µg/ml denatured, sheared salmon sperm DNA. One skilled in the art may vary conditions appropriately. Screening polynucleotides under stringent conditions may be carried out according to the method described in Nature, 313:402–404 (1985). Polynucleotide sequences capable of hybridizing under stringent conditions with the polynucleotides of the present invention may be, for example, allelic variants of the disclosed DNA sequences, or may be derived from other sources. General techniques of nucleic acid hybridization are disclosed by Sambrook et al., "Molecular Cloning: A Laboratory Manual", 2nd Ed., Cold Spring Harbor Laboratory, Cold Spring Harbor, New York (1984); and by Haymes et al., "Nucleic Acid Hybridization: A Practical Approach", IRL Press, Washington, D.C. (1985), which references are incorporated herein by reference.

The present invention provides in another embodiment: (a) an isolated and purified nucleic acid molecule comprising a sequence encoding all or a portion of a protein having the amino acid sequence as shown in SEQ ID NO:4 (clone 7B; FIG. 2B); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding a polypeptide having the amino acid sequence as shown in SEQ ID NO:6 (clone 2I; FIG. 2C); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:8 (clone 4A; FIG. 2D); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention also provides: (a) a purified and isolated nucleic acid molecule comprising a sequence as shown in SEQ ID NO:1 (FIG. 2A); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:3 (clone 7B; FIG. 2B); (b) nucleic acid sequences complementary to (a); (c) nucleic acid sequences having at least 80%, more preferably at least 90%, more preferably at least 95%, and most preferably at least 98% sequence identity to (a); or (d) a fragment of (a)

or (b) that is at least 18 bases and which will hybridize to (a) or (b) under stringent conditions.

The present invention further provides: (a) a purified and isolated nucleic acid molecule comprising a sequence as shown in SEQ ID NO:5 (clone 2I; FIG. 2C); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:7 (clone 4A; FIG. 2D); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention additionally covers nucleic acid and amino acid molecules of the present invention having one or more structural mutations including replacement, deletion or insertion mutations. For example, a signal peptide may be deleted, or conservative amino acid substitutions may be made to generate a protein that is still biologically competent or active.

The invention further contemplates a recombinant molecule comprising a nucleic acid molecule of the present invention or an oligonucleotide fragment thereof and an expression control sequence operatively linked to the nucleic acid molecule or oligonucleotide fragment. A transformant host cell including a recombinant molecule of the invention is also provided.

In another aspect, the invention features a cell or purified preparation of cells which include a novel gene encoding a CLAX protein of the present invention, or which otherwise misexpresses a gene encoding a CLAX protein of the present invention. The cell preparation can consist of human or non-human cells, e.g., rodent cells, e.g., mouse or rat cells, rabbit cells, or pig cells. In preferred embodiments, the cell or cells include a CLAX transgene, e.g., a heterologous form of a CLAX gene, e.g., a gene derived from humans (in the case of a non-human cell). The CLAX transgene can be misexpressed, e.g., overexpressed or underexpressed. In other preferred embodiments, the cell or cells include a gene which misexpresses an endogenous CLAX gene, e.g., a gene that increases expression of an endogenous CLAX gene, or a gene the expression of which is disrupted, e.g., a knockout. Such cells can serve as a model for studying disorders which are related to mutated or misexpressed CLAX alleles for use in drug screening.

Still further, the invention provides plasmids that comprise the nucleic acid molecules of the invention.

The present invention also includes a novel CLAX of the present invention, or an active part thereof. A biologically competent or active form of the protein or part thereof is also referred to herein as an "active CLAX or part thereof".

The invention further contemplates antibodies having specificity against an epitope of the CLAX protein of the present invention, or part of the protein. These antibodies may be polyclonal or monoclonal. The antibodies may be labeled with a detectable substance and they may be used, for example, to detect the novel CLAX of the invention in tissue and cells. Additionally, the antibodies of the present invention, or portions thereof, may be used to make targeted antibodies that destroy CLAX expressing cells (e.g., antibody-toxin fusion proteins, or radiolabelled antibodies).

The invention also permits the construction of nucleotide probes that encode part or all of the novel CLAX protein of the invention or a part of the protein. Thus, the invention also relates to a probe comprising a nucleotide sequence coding for a protein, which displays the properties of the novel CLAX of the invention or a peptide unique to the protein. The probe may be labeled, for example, with a detectable (e.g., radioactive) substance and it may be used to select from a mixture of nucleotide sequences a nucleotide sequence coding for a protein-which displays the properties of the novel CLAX protein of the invention.

The present invention also provides a transgenic non-human animal (e.g., a rodent, e.g., a mouse or a rat, a rabbit or a pig) or embryo all of whose germ cells and somatic cells contain a recombinant molecule of the invention, preferably a recombinant molecule comprising a nucleic acid molecule of the present invention encoding a CLAX of the invention or part thereof. The recombinant molecule may comprise a nucleic acid sequence encoding the CLAX of the present invention with a structural mutation, or may comprise a nucleic acid sequence encoding the CLAX protein of the invention or part thereof and one or more regulatory elements which differ from the regulatory elements that drive expression of the native protein. In another preferred embodiment, the animal has a CLAX gene that is misexpressed (e.g., over-expressed) or not expressed (e.g., a knockout). Such transgenic animals can serve as models for studying disorders that are related to mutated or misexpressed CLAX of the present invention.

The invention still further provides a method for identifying a substance which is capable of binding to and/or modulating the novel CLAX of the present invention, said method comprising reacting the novel CLAX of the invention or part of the protein under conditions which permit the formation of a complex between the substance and the novel CLAX protein or part of the protein, and assaying for substance-CLAX complexes, for free substance, for non-complexed CLAX, or for activation of the CLAX.

An embodiment of the invention provides a method for identifying ligands which are capable of binding to the novel CLAX protein of the invention, isoforms thereof, or part of the protein, said method comprising reacting the novel CLAX protein of the invention, isoforms thereof, or part of the protein, with at least one ligand which potentially is capable of binding to the protein, isoform, or part of the protein, under conditions which permit the formation of ligand-receptor protein complexes, and assaying for ligand-receptor protein complexes, for free ligand, for non-complexed CLAX protein, or for activation of the CLAX protein. In a preferred embodiment of the method, ligands are identified which are capable of binding to and activating or inactivating the novel CLAX protein of the invention, isoforms thereof, or part(s) of the protein.

The invention also relates to a method for assaying a medium for the presence of an agonist or antagonist of the interaction of the novel CLAX protein and a substance which is capable of binding the CLAX, said method comprising providing a known concentration of a CLAX protein, reacting the CLAX with a substance which is capable of binding to the CLAX and a suspected agonist or antagonist under conditions which permit the formation of substance-CLAX complexes, and assaying for substance-CLAX complexes, for free substance, for non-complexed CLAX, or for activation of the CLAX protein.

The invention further provides a method for identifying a substance which is capable of binding to an activated CLAX protein of the present invention or an isoform or a part of the protein, said method comprising reacting an activated CLAX of the present invention, or an isoform or part of the protein, with at least one substance which potentially can bind with the CLAX, isoform or part of the protein, under conditions which permit the formation of substance-activated CLAX complexes, and assaying for substance-CLAX complexes, for free substance, or for non-complexed CLAX. The method may be used to identify intracellular ligands containing proteins that bind to an activated CLAX protein of the present invention or parts thereof, or intracellular ligands that may be affected in other ways by the activated CLAX of the invention.

Also included within the scope of the present invention is a composition which includes a CLAX of the present invention, a fragment thereof (or a nucleic acid encoding said CLAX or fragment thereof) and, optionally, one or more additional components, e.g., a carrier, diluent or solvent. The additional component can be one that renders the composition useful for in vitro, in vivo, pharmaceutical or veterinary use.

In another aspect, the present invention relates to a method of treating a mammal, e.g., a human, at risk for a disorder, e.g., a disorder characterized by aberrant or unwanted level or biological activity of the CLAX of the present invention, or characterized by an aberrant or unwanted level of a ligand that specifically binds to a CLAX of the present invention. For example, the CLAX of the present invention may be useful to leach out or block a ligand which is found to bind to the CLAX of the present invention. Encompassed within the scope of the invention is a soluble form of the CLAX protein of the present invention, e.g., a fragment of the receptor, that may be used to inhibit activation of the receptor by binding to the ligand a polypeptide of the present invention and preventing the ligand from interacting with membrane bound CLAX.

Also within the scope of the present invention are fusion proteins comprising all or a portion of the CLAX of the present invention. Preferably, the fusion protein comprises all or a portion of the extracellular region of the CLAX of the present invention as shown in SEQ ID NO:2. All or a portion of the extracellular portion of the CLAX of the present invention may be attached to another molecule or polypeptide, e.g., a hinge and/or constant region of an immunoglobulin ("Ig") protein. Also included within the present invention are soluble fusion proteins comprising all or a portion of CLAX, and additionally comprising an extracellular domain of another receptor molecule (e.g., an extracellular domain of murine CD8 at the N-terminal side and an extracellular domain of CLAX at the C-terminal side). Examples of soluble fusion proteins are given in FIG. 4.

The primary object of the present invention is the identification of a new human CLAX, as identified by its sequence disclosed herein. Additional objects of the invention are the methods of using the cDNA, the CLAX protein, a monoclonal antibody specific for the novel CLAX, fusion proteins comprising a portion of the CLAX protein of the present invention, and a ligand for the novel CLAX as described above.

BRIEF DESCRIPTION OF THE DRAWINGS

FIG. 2A gives the nucleotide sequence (SEQ ID NO:1) and the deduced amino acid sequence (SEQ ID NO:2) of the CLAX protein of the present invention.

FIG. 2B gives the nucleotide sequence (SEQ ID NO:3) and the deduced amino acid sequence (SEQ ID NO:4) of clone 7B encoding a CLAX homologue of the present invention.

FIG. 2C gives the nucleotide sequence (SEQ ID NO:5) and the deduced amino acid sequence (SEQ ID NO:6) of clone 2I encoding a CLAX homologue of the present invention.

FIG. 2D gives the nucleotide sequence (SEQ ID NO:7) and the deduced amino acid sequence (SEQ ID NO:8) of clone 4A encoding a CLAX homologue of the present invention.

FIG. 3A is a comparison of the predicted amino acid sequences of CLAX homologues. The amino acids comprising the transmembrane region are determined by Kyte-Doolittle hydropathy plot as indicated with one solid underline. The charged arginine residue in the transmembrane region is in bold and underlined. The conserved cysteine residues are in bold. The putative N-linked glycosylation sites are underlined with two solid lines. The amino acid sequences of CLAX clone 2I (SEQ ID NO:6) and clone 4A (SEQ ID NO:8) that are different from the amino acid sequence of CLAX clone 7B (SEQ ID NO:4) are italicized.

FIG. 3B shows the amino acid sequence alignment of the C-type lectin domains of CLAX clones 7B (SEQ ID NO:15), 2I (SEQ ID NO:16) and 4A (SEQ ID NO:17) with human CD69(SEQ ID NO:18), chickein 17.5 (SEQ ID NO:19), human AICL (SEQ ID NO:20), human ASGPR (SEQ ID NO:21), human CD94, (SEQ ID NO:22) human MAFA and human CD23. Asterisks indicate conserved amino acid residues. Bold indicates the amino acid motifs that are conserved in the C-type lectin domain.

FIG. 4 shows the amino acid sequences of soluble fusion proteins of CLAX protein, designated as CLAX-8 (SEQ ID NO:12), CLAX-5 (SEQ ID NO:13) and CLAX-13 (SEQ ID NO:14). The amino acid sequences encoding for the extracellular domains of CLAX-18, -5 and -13 are in bold. The amino acid sequences of CLAX-5 and -13 which are different from the amino acid sequences of CLAX-18 are underlined.

DETAILED DESCRIPTION OF THE INVENTION

Figure 1:
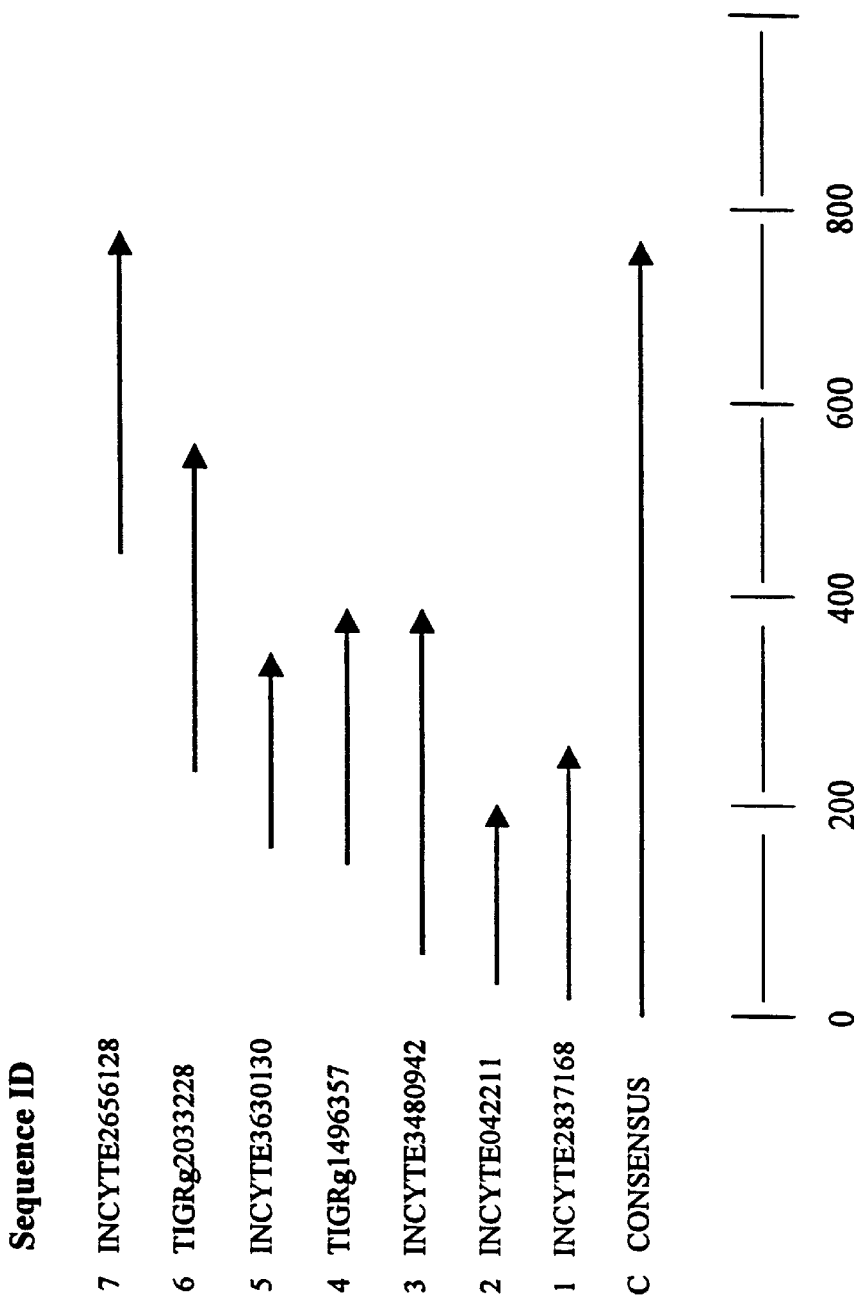
FIG. 1 is a schematic representation of the cloning strategy for the CLAX proteins of the present invention. The initial part of nucleic acid sequences coding for human CLAX was obtained by homology search of human CD69 cDNA from EST database of The Institute for Genomic Research (TIGR). Contig of ESTs was assembled by using databases from TIGR and Incyte Pharmaceuticals, Palo Alto, Calif.
Figure 5A:
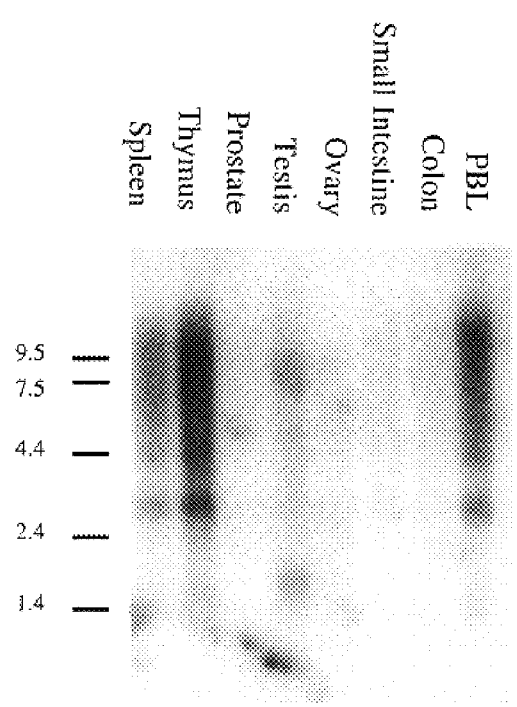
FIGS. 5A and 5B show Northern blot analysis of CLAX expression in different tissues. 2.5 µg of poly-adenylated RNA from the indicated human tissues was used to prepare Northern blots (Clontech, Palo Alto, Calif.). The blots were hybridized with a $^{32}$P labeled cDNA probe corresponding to a cDNA fragment of CLAX-18 and visualized by autoradiography. Position of RNA standards is indicated on the left in kb. Two transcripts of approximately 2.5 kb and 4.0 kb are indicated by arrows on the right. The transcripts were detected in lymphoid tissues (with the exception of bone marrow and fetal liver) and not detected in non-lymphoid tissues (prostate, testis, ovary, small intestine and colon).
Figure 5B:
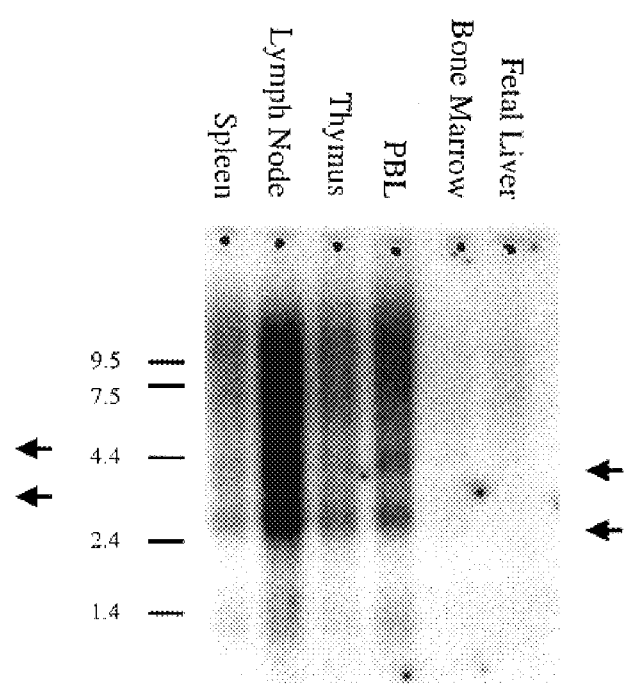

The present invention provides a nucleic acid and amino acid sequence of a novel CLAX protein, as well as the nucleic acid and amino acid sequences of three CLAX homologues.

The nucleic acids of the present invention can be used in a variety of ways in accordance with the present invention. For example, they can be used as DNA probes to screen other cDNA and genomic DNA libraries so as to select by hybridization other DNA sequences that code for proteins related to CLAX and its variants. In addition, the nucleic acids of the present invention can be used as DNA probes to screen other cDNA and genomic DNA libraries to select by hybridization other DNA sequences that code for proteins of CLAX and its variants from other organisms. The nucleic acid probes can be RNA or DNA, and may or may not be labeled with radioactive nucleotides, or may be used in non-radioactive methods (i.e., biotin). Screening can be done at various stringency conditions (through manipulation of the hybridization Tm, usually using a combination of ionic strength, temperature and/or presence of formamide) to isolate close or distantly related homologues. Stringency conditions under which a nucleic acid sequence of at least 18 nucleic acids from SEQ ID NO:1 would hybridize to the nucleic acid sequences disclosed herein are, for example, 50% formamide, 5×SSPE (750 mM NaCl, 50 mM NaH$_2$PO$_4$ and 5 mM EDTA), 5×Denhardt's solution, 0.1% SDS and 100 μg/ml denatured, sheared salmon sperm DNA.

The nucleic acids may also be used to generate primers to amplify cDNA or genomic DNA using polymerase chain reaction (PCR) techniques. The nucleic acid sequences of the present invention can also be used to identify adjacent sequences in the cDNA elements. In addition, the nucleic acid sequences of the present invention can be used diagnostically to detect nucleic acid sequences encoding CLAX and its variants in diseases of inflammation and allergy. Detection of such mutations can be determined by standard DNA analysis techniques, including genomic and/or cDNA sequencing, SSCP and Southern blot.

The nucleic acid sequences encoding CLAX and the homologues disclosed herein provide the means for obtaining CLAX protein, a homologue thereof, and/or a soluble form of CLAX and its homologues/variants. The polypeptides and soluble forms of CLAX of the present invention are useful in the study of the characteristics of CLAX, for example, its structure, mechanism of action, and role in inflammation and allergy. The soluble form of CLAX and its variants can be used to generate monoclonal and polyclonal antibodies. The CLAX proteins and its homologues can be detected using monoclonal and polyclonal antibodies for diagnosis of diseases of inflammation and allergy by using ELISA, immunoprecipitation, immunohistochemistry, or Western blot analysis. CLAX proteins can be studied to further delineate functional domains, and thus can be used to model compounds with similar activity. In addition, the CLAX protein and homologues disclosed herein can be used in in vivo cell based and in in vitro cell free assays to screen natural products and synthetic compounds that might mimic, regulate or otherwise modulate (e.g., agonists and/or antagonists) CLAX protein function.

Various other methods of using the nucleic acids and polypeptides of the present invention are described in detail below.

Nucleic Acids

The present invention provides a nucleic acid sequence encoding a novel CLAX protein, as well as nucleic acid sequences for three CLAX homologues. Preferably, the nucleic acid molecule is a DNA molecule. A preferred embodiment of the invention provides a nucleic acid sequence (SEQ ID NO:1) comprising nucleotides 6 through 587 of the sequence shown below (SEQ ID NO:9):

GCAAA ATG CAT GAC AGT AAC AAT GTG GAG AAA GAC ATT ACA 41
CCA TCT GAA TTG CCT GCA AAC CCA GGT TGT CTG CAT TCA AAA 83
GAG CAT TCT ATT AAA GCT ACC TTA ATT TGG CGC TTA TTT TTC 125
TTA ATC ATG TTT CTG ACA ATC ATA GTG TGT GGA ATG GTT GCT 167
GCT TTA AGC GCA ATA AGA GCT AAC TGC CAT CAA GAG CCA TCA 209
GTA TGT CTT CAA GCT GCA TGC CCA GAA AGC TGG ATT GGT TTT 251
CAA AGA AAG TGT TTC TAT TTT TCT GAT GAC ACC AAG AAC TGG 293
ACA TCA AGT CAG AGG TTT TGT GAC TCA CAA GAT GCT GAT CTT 335
GCT CAG GTT GAA AGC TTC CAG GAA CTG AAT TTC CTG TTG AGA 377
TAT AAA GGC CCA TCT GAT CAC TGG ATT GGG CTG AGC AGA GAA 419
CAA GGC CAA CCA TGG AAA TGG ATA AAT GGT ACT GAA TGG ACA 461
AGA CAG TTA GTC ATG AAA GAA GAT GGT GCC AAC TTG TAT GTT 503
GCA AAG GTT TCA CAA GTT CCT CGA ATG AAT CCA AGA CCT GTC 545
ATG GTT TCC TAT CCT GGG AGC AGG AGA GTG TGC CTA TTT GAA 587
TGACAAAGGT GCCAGTAGTG CCAGGCACTA CACAGAGAGG AAGTGGATTT 637
GTTCCAAATC AGATATACAT GTCTAGATGT TACAG-CAAAG CCCCAACTAA 687
TCTTTAGAAG CATATTGGAA CTGATAACTC CATTT-TAAAA TGAGCAAAGA 737
ATTTATTTCT TATACCAACA GGTATATGAA AATAT-GCTCA ATATCACTAA 787
TAACTGGGAA AATACAATCA AAATCATAGT AAAATATTAC CTGTTTTCAT 837
GGTGCTAATA TTACCTGTTC TCCCACTGCT AATGA-CATAC CCGAGACTGA 887
GTAATTTATA AATAAAAGAG ATTTAATTGA AAAAAAAAAA 931

Also within the scope of the present invention are nucleic acid sequences encoding homologues of the CLAX protein, for example the nucleic acid sequence of CLAX clone 7B (SEQ ID NO:3), the nucleic acid sequence of CLAX clone 2I (SEQ ID NO:5), and the nucleic acid sequence of CLAX clone 4A (SEQ ID NO:7). Preferred are the coding regions of the above referenced sequences.

Also encompassed within the scope of the present invention are nucleic acid sequences complementary to one of these nucleic acid sequences. Additionally preferred are nucleic acid sequences that hybridize to one of these nucleic acid sequences. In the case of nucleotide sequences (e.g., a DNA sequence) that will hybridize to the sequences provided herein coding for CLAX and its homologues, it is preferred that the nucleotide sequence be at least about 15 sequential nucleotides in length, more preferably about 18 sequential nucleotides in length, more preferably at least about 20 to 30 sequential nucleotides in length (said sequential nucleotides contained in SEQ ID NO:1, SEQ ID NO:3, SEQ ID NO:5, SEQ ID NO:7, or SEQ ID NO:9).

Also within the present invention are nucleic acid sequences that differ from the nucleic acid sequences disclosed herein due to degeneracy of the genetic code (i.e., nucleic acid sequences that encode amino acid sequences identical to the amino acid sequences encoded by the nucleic acid sequences provided herein).

The nucleic acids of the present invention can be isolated from a variety of sources, although the presently preferred sequences have been isolated from a human cDNA library. The exact amino acid sequences of the polypeptide molecules produced will vary with the initial DNA sequences.

The nucleic acids of the present invention can be obtained using various methods well known to those of ordinary skill in the art, for example, but not limited to, the following methods: (1) the isolation of double-stranded DNA sequence from genomic DNA or complementary DNA (cDNA) which contains the sequences; (2) the chemical synthesis of the DNA sequences; and (3) the synthesis of the DNA sequences by polymerase chain reaction (PCR).

In the first method, a genomic or cDNA library can be screened in order to identify a DNA sequence coding for all or part of CLAX and/or its homologues. Various techniques can be used to screen genomic DNA or cDNA libraries for sequences that code for novel CLAX proteins. This technique may, for example, employ a labeled single-stranded DNA probe with a sequence complementary to a sequence that codes for CLAX. For example, DNA/DNA hybridization procedures may be used to identify the sequence in cloned copies of genomic DNA or cDNA that have been denatured to a single-stranded form. Suitable probes include cDNA for CLAX and its variants acquired from the same or a related species, synthetic oligonucleotide, and the like. A genomic or cDNA library can be screened in order to identify a DNA sequence coding for sequences flanking such coding sequences, using immunoblotting techniques.

In one typical screening method suitable for the hybridization techniques, a genomic DNA or cDNA library is first spread out on agar plate, and then the clones are transferred to filter membranes, for example, nitrocellulose membranes. The genomic library is usually contained in a vector such as EMBL 3 or EMBL 4 or derivatives, or in cosmid libraries, P1 phage libraries or YAC libraries. The cDNA library is usually contained in a vector such as λgt10, λgt11, or λZap. A DNA probe can then be hybridized to the clones to identify those clones containing the gemonic DNA or cDNA coding for all or part of CLAX and its homologues. Alternatively, appropriate *E. coli* strains containing vectors such as λgt11 or λZap can be induced to synthesize fusion proteins containing fragments of proteins corresponding to the cDNA insert in the vector. The fusion proteins may be transferred to filter membranes, for example, nitrocellulose. An antibody may then be bound to the fusion protein to identify all or part of CLAX and/or its homologues.

In a second method, the nucleic acids of the present invention coding for CLAX and its variants can be chemically synthesized. Shorter oligonucleotide, such as 15 to 50 nucleotides, may be directly synthesized. For longer oligonucleotides, the DNA sequence coding for CLAX and/or its homologues can be synthesized as a series of 50–100 base oligonucleotides that can then be sequentially ligated (via appropriate terminal restriction sites) so as to form the correct linear sequence of nucleotides.

In a third method, the nucleic acids of the present invention coding for CLAX and/or its homologues can be synthesized using PCR. Briefly, pairs of synthetic DNA oligonucleotides, generally at least 15 bases in length (PCR primers) that hybridize to opposite strands of the target DNA sequence, are used to enzymatically amplify the intervening resign of DNA on the target sequence. Repeated cycles of heat denaturation of the template, annealing of the primers and extension of the 3'-termini of the annealed primers with a DNA polymerase, result in amplification of the segment defined by the PCR primers.

The nucleic acids of the present invention coding for CLAX and its homologues can also be modified (i.e., mutated) to prepare various additional biologically active analogues of CLAX or its homologues disclosed herein. Such mutations may change the amino acid sequence encoded by the mutated codon, or they may be silent and not change the amino acid sequence. These modified nucleic acids may be prepared, for example, by mutating the nucleic acids coding for CLAX and its homologues so that the mutation results in the deletion, substitution, insertion or addition of one or more amino acids in the encoded polypeptide using various methods known in the art. For example, the methods of site-directed mutagenesis may be employed. In addition, kits for site-directed mutagenesis may be purchased from commercial vendors. Disruption, deletion and truncation methods may also be employed. Mutations may be advantageous in producing or using the polypeptides of the present invention. For example, these mutations may modify the function of the protein (e.g. result in higher of lower activity), permit higher levels of protein production of easier purification of the protein, or provide additional restriction endonuclease recognition sites in the nucleic acids. All such modified nucleic acid and polypeptide molecules are included within the scope of the present invention. As used in the present application, unless otherwise limited in specific instances, the term "modified", when referring to a nucleotide or polypeptide sequence, means a nucleotide or polypeptide sequence which differs from the wild-type sequence found in nature.

Expression Vectors

The present invention further concerns expression vectors comprising a DNA sequence coding for all or part of CLAX and its homologues. The expression vectors preferably contain all or part of the DNA sequences having the nucleotide sequences shown in FIGS. 2A–2D (SEQ ID NO:1; SEQ ID NO:3; SEQ ID NO:5; SEQ ID NO:7; and SEQ ID NO:9). Further preferred are expression vectors comprising one or more regulatory DNA sequences operatively linked to the DNA sequence coding for all or part of the CLAX and its variants. As used in this context, the term "operatively linked" means that the regulatory DNA sequences are capable of directing the replication and/or the expression of the DNA sequence coding for all or part of CLAX and/or its homologues.

Expression vectors of utility in the present invention are often in the form of "plasmids", which refer to circular double stranded DNA loops that, in their vector form, are not bound to the chromosome. However, the invention is intended to include such other forms of expression vectors which serve equivalent functions and which become known in the art subsequently hereto. The expression vectors of the present invention may also be used for the stable integration of the DNA sequence encoding CLAX or its homologues into the chromosome of an appropriate host cell (e.g. CHO, Jurkat and EB cells).

Expression vectors useful in the present invention typically contain an origin of replication, a promoter located 5' to (i.e., upstream of) and followed by the DNA sequence coding for all or part of CLAX and/or its homologues, transcription termination sequence, and the remaining vector. The expression vectors may also include other DNA sequence known in the art, for example, stability leader sequences that provide for stability of the expression product, secretory leader sequences which provide for secretion of the expression product, sequences which allow expression of the structural gene to be modulated.

Gene constructs of the present invention can also be used as part of a gene therapy protocol to deliver nucleic acids encoding CLAX and/or a homologue thereof of the present invention, or an agonist or antagonist form of a CLAX protein or peptide. The invention features expression vectors for in vivo transfection and expression of a CLAX protein. Expression constructs of the CLAX protein of the present invention, may be administered in any biologically effective carrier, e.g., any formulation or composition capable of effectively delivering the CLAX gene to cells in vivo. Approaches include insertion of the subject gene in viral vectors including recombinant retroviruses, adenoviruses, adeno-associated viruses, and herpes simplex virus-1, or recombinant bacterial or eukaryotic plasmids. Viral vectors transfect cells directly; an advantage of infection of cells with a viral vector is that a large proportion of the targeted cells can receive the nucleic acid. Several viral delivery systems are known in the art and can be utilized by one practicing the present invention.

In addition to viral transfer methods, non-viral methods may also be employed to cause expression of the CLAX gene in the tissue of an animal. Most non-viral methods of gene transfer rely on normal mechanisms used by mammalian cells for the uptake and intracellular transport of macromolecules. Exemplary gene delivery systems of this type include liposomal derived systems, poly-lysine conjugates, and artificial viral envelopes. DNA of the present invention may also be introduced to cell(s) by direct injection of the gene construct or electroporation.

In clinical settings, the gene delivery systems for the therapeutic CLAX gene can be introduced into a patient by any of a number of methods, each of which is known in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

Another aspect of the invention relates to the use of an isolated nucleic acid in "antisense" therapy. As used herein, "antisense" therapy refers to administration or in situ generation of oligonucleotides or their derivatives which specifically hybridize under cellular conditions, with the cellular mRNA and/or genomic DNA encoding CLAX or homologue thereof of the present invention so as to inhibit expression of the encoded protein, e.g., by inhibiting transcription and/or translation. In general, "antisense" therapy refers to the range of techniques generally employed in the art, and includes any therapy which relies on specific binding to oligonucleotide sequences.

Polypeptides

The present invention further encompasses polypeptide molecules comprising all or a portion of CLAX and/or its homologues, said polypeptide molecules preferably having all or part of the amino acid sequence as shown in FIG. 2A (SEQ ID NO:2) and FIG. 3 (SEQ ID NO:4; SEQ ID NO:6; and SEQ ID NO:8). In the case of polypeptide molecules comprising part of CLAX and/or a homologue thereof, it preferred that polypeptide molecules be at least about 5 to 8 sequential amino acids in length, more preferably at least about 15 to 20 sequential amino acids in length.

All amino acid sequences are represented herein by formulas whose left to right orientation is in the conventional direction of amino-terminus to carboxy-terminus.

Polypeptides of the present invention may be obtained by synthetic means, i.e., chemical synthesis of the polypeptide from its component amino acid, by methods known to those of ordinary skill in the art. For example, the solid phase procedure may be employed. The polypeptides may also be obtained by production in prokaryotic or eukaryotic host cells expressing a DNA sequence coding for all or part of CLAX and/or a homologue thereof. The polypeptides may be translated in vitro from mRNA encoded by a DNA sequence coding for all or part of CLAX and/or a homologue thereof. For example, the nucleotide sequence as shown in SEQ ID NO:1 may be synthesized using PCR as described above and inserted into a suitable expression vector, which in turn may be used to transform a suitable host cell. The recombinant host cell may then be cultured to produce CLAX and/or its homologues. Techniques for the production of polypeptides by these means are known in the art, and are described herein.

The polypeptides produced in this manner may then be isolated and purified to some degree using various protein purification techniques. For example, chromatographic procedures such as ion exchanges, gel filtration and immunoaffmity may be employed.

The polypeptides of the present invention may be used in wide variety of ways. For example, the polypeptides may be used to prepare in a known manner polyclonal or monoclonal antibodies capable of binding the polypeptides. These antibodies may in turn be used for the detection of the polypeptides of the present invention in a sample (e.g., a cell sample) using immunoassay techniques, radioimmunoassay, enzyme immunoassay, or immunocytochemistry. The antibodies may also be used in affinity chromatography for isolating or purifying the polypeptides of the present invention from various sources.

The polypeptides of the present invention have been defined by means of determined DNA and deduced amino acid sequencing. Due to the degeneracy of the genetic code, other DNA sequences which encode the same amino acid sequences depicted in FIG. 2 and FIG. 3, or any part thereof, may be used for the production of the polypeptides of the present invention.

The present invention further relates to CLAX protein and homologues thereof which have the amino acid sequences encoded by the deposited cDNA clones, as well as fragments, analogs and derivatives of such polypeptide. Encompassed within the scope of the present invention are polypeptides as shown in SEQ ID NO:4, SEQ ID NO:6 and SEQ ID NO:8.

The deposit(s) referred to herein will be maintained under the terms of the Budapest Treaty on the International Recognition of the Deposit of Micro-Organisms for purposes of Patent Procedure. These deposits are provided merely as convenience to those of skill in the art and are not an admission that a deposit is required under 35 U.S.C. §112. The sequence(s) of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

Analogs of the novel CLAX protein and homologues disclosed herein are also within the scope of the present invention. Analogs can differ from the naturally occurring proteins of the present invention in amino acid sequence or in ways that do not involve sequence, or both. Non-sequence modifications include in vivo or in vitro chemical derivitization of the CLAX proteins of the present invention. Non-sequence modifications include changes in acetylation, methylation, phosphorylation, carboxylation, or glycosylation.

Preferred analogs include the novel CLAX and homologue proteins of the present invention (or biologically active fragments thereof) whose sequences differ from the wild-type sequence by one or more conservative amino acid substitutions or by one or more non-conservative amino acid substitutions, deletions or insertions which do not abolish the biological activity of the proteins of the present invention. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

Other contemplated variations include salts and esters of the aforementioned polypeptides, as well as precursors of the aforementioned polypeptides, for example, precursor having N-terminal substituents such as methionine, N-formylmethionine and leader sequences. All such variations are included within the scope of the present invention.

The present invention also relates to methods of screening. Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case binding of a ligand to the CLAX proteins of the present invention. Techniques known in the art are amenable to high through-put analysis for screening large numbers of sequences created, e.g., by random mutagenesis techniques.

Two hybrid assays can be used to identify fragments or analogs of a protein or peptide which bind to the CLAX protein or homologues of the present invention. These may include agonists or antagonists. In one approach to screening assays, the candidate protein or peptides are displayed on the surface of a cell or viral particle, and the ability of particular cells or viral particles to bind an appropriate receptor protein via the displayed product is detected in a "panning assay". In a similar fashion, a detectably labeled ligand can be used to score for potentially functional peptide homologues. Fluorescently labeled ligands, e.g., receptors, can be used to detect homologue which retain ligand-binding activity. The use of fluorescently labeled ligand allows cells to be visually inspected and separated under fluorescence microscope or to be separated by a fluorescence-activated cell sorter.

High through-put assays can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between the CLAX of the present invention and its respective ligand can be used to identify antagonists from a group of peptide fragments isolated through one of the primary screens. Therefore, methods for generating fragments and analogs and testing them for activity are known in the art. Once a sequence of interest is identified, it is routine for one skilled in the art to obtain agonistic or antagonistic analogs, fragments, and/or ligands.

Drug screening assays are also provided in the present invention. By producing purified and recombinant CLAX of the present invention, or fragments thereof, one skilled in the art can use these to screen for drugs which are either agonists or antagonists of the normal cellular function or their role in cellular signaling. In one embodiment, the assay evaluates the ability of a compound to modulate binding between the CLAX of the present invention and a naturally occurring ligand. The term "modulating" encompasses enhancement, diminishment, activation or inactivation of the CLAX protein. Assays useful to identify ligands to the CLAX protein of the present invention, including peptides, proteins, small molecules, and antibodies that are capable of binding to the CLAX protein are encompassed herein. A variety of assay formats will suffice and are known by those skilled in the art.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as primary screens in that they can be generated to permit rapid development and relatively easy detection of an alteration in a molecular target which is mediated by a test compound.

Also within the scope of the present invention is a process for modulating the CLAX protein of the present invention. Ligands to the CLAX protein of the present invention, including peptides, proteins, small molecules, and antibodies, that are capable of binding to the CLAX receptor and modulating its activity are encompassed herein. These compounds are useful in modulating the activity of the CLAX protein and in treating CLAX-associated disorders. "CLAX-associated disorders" refers to any disorder or disease state in which the CLAX protein plays a regulatory role in the metabolic pathway of that disorder or disease. Such disorders or diseases may include infection, autoimmune diseases and allergy. As used herein the term "treating" refers to the alleviation of symptoms of a particular disorder in a patient, the improvement of an ascertainable measurement associated with a particular disorder, or the prevention of a particular immune, inflammatory or cellular response (such as transplant rejection).

The invention also includes antibodies specifically reactive with the CLAX protein of the present invention, or a portion thereof. Anti-protein/anti-peptide antisera or monoclonal antibodies can be made by standard known procedures. A mammal such as a mouse, a hamster or rabbit can be immunized with an immunogenic form of the polypeptide. Techniques for conferring immunogenicity on a protein or peptide include conjugation to carriers or other techniques known in the art. An immunogenic portion of the CLAX of the present invention can be administered in the presence of adjuvant. The progress of immunization can be monitored by detection of antibody titers in plasma or serum.

The term "antibody" as used herein is intended to include fragments thereof which are also specifically reactive with the CLAX protein and/or homologues of the present invention. Antibodies can be fragmented using conventional techniques and the fragments screened for utility in the same manner as whole antibodies. For example, F(ab')2 fragments can be generated by treating antibody with pepsin. The resulting F(ab')2 fragment can be treated to reduce disulfide bridges to produce Fab' fragments. The antibody of the present invention is further intended to include chimeric and humanized molecules that recognize and bind to the CLAX proteins of the present invention.

Both monoclonal and polyclonal antibodies directed against the CLAX proteins of the present invention, and antibody fragments such as Fab', sFv and F(ab')2, can be used to block the action of the CLAX proteins of the present invention and allow study of the role of a particular CLAX or homologue of the present invention. Alternatively, such antibodies can be used therapeutically to block the CLAX protein of the present invention in a subject mammal, e.g., a human. In a preferred embodiment therapeutic compositions comprising an antibody of the present invention can also comprise a pharmaceutically acceptable carrier, solvent or diluent, and be administered by systems known in the art.

Antibodies of the present invention may also be useful as potential agonists of the CLAX proteins of the present invention. Such agonistic antibodies tend to aggregate and crosslink the receptor, which induces signaling, proliferation, differentiation and/or cell death (apoptosis).

Antibodies that specifically bind to the CLAX proteins of the present invention, or fragments thereof, can also be used in immunohistochemical staining of tissue samples in order to evaluate the abundance and pattern expression of the CLAX of the present invention. Antibodies can be used diagnostically in immunoprecipitation, immunoblotting, and enzyme linked immunosorbent assay (ELISA) to detect and evaluate levels of the CLAX proteins of the present invention in tissue or bodily fluid.

The following examples further illustrate the present invention. These examples are not intended to limit the scope of the present invention, and may provide further understanding of the invention.

EXAMPLE I

Identification of Novel CLAX and Its Variants

1. Bioinformatics

CD69 is widely expressed on hematopoietic cells including lymphocytes, neutrophils, eosinophils, platelets and epidermal langerhans cells. It is not expressed on resting but is rapidly induced upon activation. CD69 is the earliest activation marker of lymphocytes. Anti-CD69 mAb can induce activation and cytokine production of T, B and NK cells. These functions may shed light on its homologues.

A full-length polypeptide sequence of human CD69 was used as a query sequence searching for nucleotide sequences (six-frame translations) against TIGR Expressed Sequence Tag (EST) database. Two relevant ESTs from activated T cells were identified by doing TBLASTN software program (Basic Local Alignment Search Tool). The ESTs were retrieved using ENTREZ. The retrieved ESTs were imported into the LifeSeq program of Incyte Pharmaceuticals and used as query nucleotide sequences searching for Incyte EST database. Five more ESTs were identified by using TBLASTX software program. The 7 ESTs were assembled into a single contiguous project (Contig) by using GCG assembly software (FIG. 1). The contig cDNA encodes a novel type II membrane protein and belongs to the C-type lectin superfamily (FIG. 2A). Its deduced amino acid sequence is 41% amino acid identical to those of human CD69, the closest one in amino acid sequence. This novel cDNA was labeled as "CLAX" protein by the inventors.

2. PCR Cloning of Extracellular Domain of CLAX

According to nucleotide sequence of the CLAX contig, the sense primer oligonucleotide (5'-CTAGGATCCAAGAGCTAACTGCCATCAAGAGCC-3') (SEQ ID NO:10) with a restriction site for BamHI and the antisense primer (5'-CATTCTAGATGCCTGGCACTACTGGCACCTTTG-3') (SEQ ID NO:11) with a restriction site for XbaI were synthesized by Life Technologies, Gaithersburg, Md. A DNA fragment encoding for the extracellular domain of CLAX was amplified by reverse transcription-coupled PCR from RNA prepared from LPS-activated human THP-1 cells. The PCR product was cloned directly into the vector CDM7B-, which contains cDNA of the extracellular domain of mouse CD8 in upstream of the restriction site for BamHI. The inserted DNA in the CDM7B-CLAX construct (CLAX-18) was sequenced in both strands by the dideoxy chain termination method and is identical to DNA segment of the contig of CLAX.

3. Isolation of cDNA Encoding CLAX and its Variants

A λ TriplEx cDNA library derived from human leukocytes was purchased from Clontech, Palo Alto, Calif. The library was screened with [$^{32}$P] dCTP random prime-labeled DNA probe that was generated by purification of the BamHI-XbaI cDNA fragment from CLAX-18 construct. The nylon transfer membranes were hybridized in hybridization solution 1 at 42° C. for 16 h according to the manufacturer's recommendations. After hybridization, the membranes were washed with 3 changes in 2×SSC and 0.1% SDS for 30 min at room temperature and then in 1×SSC and 0.1% SDS for 60 min at 65° C. The positive plaques were plated and screened for second round hybridization with the same CLAX-18-specific DNA probe. The positive λ TriplEx plaques were further converted into plasmid clones of pTriplEx in different host *E. coli* provided by Clontech. The cDNAs from isolated pTriplEx were sequenced in both strands by the dideoxy chain termination method. Three clones encoding different extracellular domains of CLAX were identified. Clone 7B encodes the sequence that matches to the contig of CLAX. Clone 2I has a frame-shift in its ORF, resulting in a different polypeptide from clone 7B at the last 37 amino acid residues of C-terminal. Clone 4A contains a truncation within its extracellular domain. The parts of DNA sequence of clone 7B, clone 2I and clone 4A match to the DNA sequences of clones isolated by PCR cloning. Since all three forms of CLAX can be produced by both screen of cDNA library and PCR cloning, the results suggest that CLAX and its homologues naturally exist. The different forms of cDNA may be due to the result of alternative splicing.

4. Determination of the CLAX cDNA Sequence

The complete nucleotide sequence (SEQ ID NO:9) of the CLAX cDNA is depicted in FIG. 2A. An open reading frame deduced from the nucleotide sequence starts at nucleotide #6 with a codon for methionine and ends at nucleotide #587 before a TGA stop codon (SEQ fD NO:1 gives the reading frame). The Kyte-Doolittle Hydropathy plot of the deduced amino acid sequence predicts a 26 amino acid long transmembrane domain (FIG. 3A, underlined). A positively charged arginine residue is located within the transmembrane domain. There are two putative N-glycosylation sites in clone 7B and clone 2I and there is one putative N-glycosylation site in clone 4A.

A search for homology to the CLAX cDNA nucleotide sequences indicated that the CLAX and its homologues are novel unknown genes. However, significant homology was found between the extracellular domain of CLAX-7B, 2I and 4A and the carbohydrate recognition domain (CRD) of several type II integral membrane proteins that are members of the $Ca^{2+}$-dependent C-type lectin superfamily. Among them, human CD69 is the closest one with 41% amino acid identical to that of human CLAX-7B. Chicken17.5 is the closest one for CLAX-2I and 4A with 35% and 25% amino acid identity, respectively. Interestingly, these C-type lectins displaying high sequence homology with the CLAX CRD are all involved in immunological functions. Most of these genes are located in the NK gene complex at human chromosome 12. Besides CD69 and Chicken17.5, these are the activation-induced C-type lectin (AICL), asialoglycoprotein, CD94, Mast cell function-associated antigen (MAFA), the type II receptor for IgE (Fcε-RII/CD23) and the natural killer antigens Ly-49. Amino acid sequence alignment of the CFD of the CLAX and of several of the above-mentioned lectins shows the absolute conservation of 11 residues (4 tryptophans, 3 cysteines, and 2 glycines and 2 leucines) interspersed within this 76 to 79 amino acids long domain (FIG. 3B). Furthermore, the WIGL and CFYFS amino acid motifs are highly conserved throughout these proteins.

EXAMPLE II

Cloning and Expression of the Fusion Proteins of CLAX and its Variants

1. Construction of the Fusion Proteins of CLAX and its Variants

DNA fragments encoding the extracellular domain of CLAX and its variants, which are CLAX-18, CLAX-13 and CLAX-5, were amplified by reverse transcription-coupled PCR as described above. The PCR products were cloned directly into the vector CDM7B-, which contains cDNA of the extracellular domain of mouse CD8 (mCD8) upstream of the BamHI insertion site. As shown in FIG. 4, the resulting constructs encode soluble fusion protein with mCD8 at the side of N-terminal and CLAX at the side of C-terminal. The inserted DNA segments in CDM7B- constructs were sequenced in both strands by the dideoxy chain termination method.

2. Transfection

The CDM7B-CLAX and its variant constructs were transiently transfected into COS-7 cells by the DEAE-dextran precipitation technique. Briefly, 75% confluent COS-7 cells were incubated in 5% NuSerum DMEM medium with mixture of DEAE-dextran/DNA for 3 hours and then shocked with 10% DMSO in PBS for 2 min. The cells were cultured in 10% FCS DMEM medium at 37° C. overnight and then in serum-free DMEM medium for additional 7 days. Supernatant was collected for further analysis and purification.

3. Detection of Fusion Proteins by Enzyme-linked Immunosorbent Assay (ELISA) and Western Blot The methods used here are designed to detect the mCD8 portion of the fusion proteins. The expression of CLAX fusion proteins in supernatant was first examined by ELISA. Briefly, Dynatech Immunon II 96-well plates were coated with 2 μg/ml of monoclonal antibody (mAb) 53.6 against mCD8 in carbonate/bicarbonate buffer (pH 9.6) for overnight at 4° C. The plates were blocked with LAV EIA specimen diluent for 1 hour and washed three times with PBS/Tween buffer. The supernatant samples at 100 μl per well were added and incubated for 1 hour at room temperature. After incubation, the plates were washed and then 2 μg/ml of biotinylated detecting mAb 53.6 were added into the well. The samples were read out by color reaction, which is mediated by avidin-conjugated peroxidase added in the well. The supernatant samples and purified fusion proteins were also detected with mAb 53.6 by Western blot. Discontinuous SDS-PAGE was performed using 14% polyacrylamide gels.

4. Purification of Fusion Proteins of CLAX and its Variants

The immunoaffinity columns were generated by immobilization of mAb 53.6 against mCD8 onto the protein-G sepharose beads. The 53 .6-coaded beads were covelantly linked by the chemical linker DMPI (Pierce) and quenched in 0.2M ethanolamine (pH 8). Before loading sample onto the column, the beads were washed three times in PBS. The supernatants of CLAX-18, CLAX-13 and CLAX-5 were loaded onto the three individual columns, respectively. The columns were washed with 100 bed volumes of PBS. The fusion proteins of CLAX-18, CLAX-13 and CLAX-5 were eluted from the columns with elution buffer (35% propylene glycol in PBS containing 1.25 M ammonium sulfate, 20 mM Hepes, 0.05% Azide).

EXAMPLE III

Expression of Genes of CLAX and Its Variants

1. Isolation of RNA and Northern Blot Analysis

25 μg of total RNA was subjected to electrophoresis through a denaturing 1.2% agarose, 5% formaldehyde gel and transferred to an Optitran nitrocellulose membrane (Schleicher & Schuell, Keene, N.H.). Equal loading of samples was confirmed by staining RNA with ethidium bromide. Human tissue mRNA blots were purchased from Clontech. Human CLAX-specific probe was generated by purification of the BamHI-XbaI cDNA fragment and labeled with [$^{32}$P] dCTP by using random prime-labeling kit. The membranes were hybridized in ExpressHyb solution at 68° C. for 60 min. After hybridization, the membranes were washed with 3 changes in 2×SSC and 0.1% SDS for 30 min at room temperature, and then in 1×SSC and 0.1% SDS for 60 min at 65° C.

Figure 6:
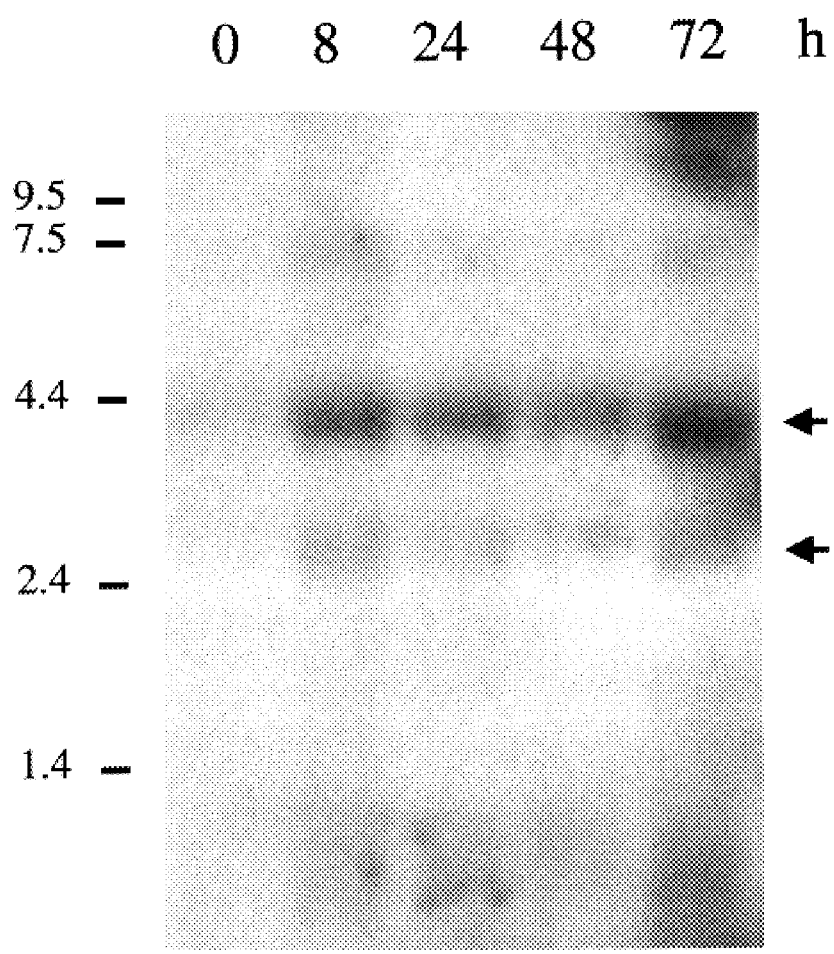
FIG. 6 shows a Northern blot analysis of transcription kinetics of CLAX gene during T lymphocyte activation. Human T lymphocytes were activated by immobilized anti-CD3 mAb. 25 µg of total RNA from the indicated time point of activation was loaded at each lane in a Northern blot. The RNA were subjected to electrophoresis through a denaturing 1.2% agarose, 6% formaldehyde gel and transferred to an Optitran nitrocellulose membrane. The blots were hybridized with a $^{32}$P labeled cDNA probe corresponding to a cDNA fragment CLAX-18 and visualized by autoradiography. Position of RNA standards is indicated on the left in kb. Two transcripts of approximately 2.5 kb and 4.0 kb were detected in activated T lymphocytes (8, 24, 48 and 72 hours) but not in resting T lymphocytes (0 hour).

2. Isolation T Lymphocytes from Peripheral Blood Mononuclear Cells and Generation of Antigen-nonspecific Activated T Lymphocytes Peripheral blood mononuclear cells (PBMC) were obtained by using Ficoll-Hypaque density gradient centrifugation from three healthy donors. The PBMC were mixed with sheep red blood cells (SRBC) and spun at 1000 rpm for 5 min. The pellet was incubated on ice for 1 hour and followed by gentle resuspension with medium. The mixture of PBMC-SRBC was spun again with Ficoll-Hypaque density gradient. The SRBC-rosetted T lymphocytes in pellet were isolated by removing SRBC with hypotonic lysis. After washing twice with PBS, the T lymphocytes without incubation were referred as resting T cells (0 hour in FIG. 6). The rest of the T lymphocytes were incubated in 6-well plates that were coated with anti-CD3 monoclonal antibody (G19-4). The cells were harvested at the different time point (8, 24, 48 and 72 hours in FIG. 6). The total RNA of each sample was prepared and subjected to Northern blot analysis.

Although the present invention has been described in some detail by way of illustration and example for purposes of clarity and understanding, it will be apparent that certain changes and modifications may be practiced within the scope of the appended claims.

We claim:

1. A purified and isolated nucleic acid sequence encoding a CLAX (C-type Lectin, Activation Expressed) protein, said CLAX protein comprising the amino acid sequence as shown SEQ ID NO:2.

2. The nucleic acid sequence of claim 1 comprising (a) the nucleic acid sequence as shown in SEQ ID NO:1; (b) the complement of (a); or (c) a nucleic acid sequence that differs from (a) or (b) due to the degeneracy of the genetic code.

3. A purified and isolated nucleic acid sequence encoding a CLAX (C-type Lectin, Activation Expressed) protein homologue, said CLAX protein homologue comprising the amino acid sequence as shown in SEQ ID NO:4.

4. The nucleic acid sequence of claim 3 comprising (a) the nucleic acid sequence as shown in SEQ ID NO:3; (b) the complement of (a); or (c) a nucleic acid sequence that differ from (a) or (b) due to degeneracy of the genetic code.

5. A purified and isolated nucleic acid sequence encoding a CLAX (C-type Lectin, Activation Expressed) protein homologue, said CLAX protein homologue comprising the amino acid sequence as shown in SEQ ID NO:6.

6. The nucleic acid sequence of claim 5 comprising the nucleic acid sequence as shown in SEQ ID NO:5; (b) the complement of (a); or (c) a nucleic acid sequence that differs from (a) or (b) due to degeneracy of the genetic code.

7. A purified and isolated nucleic acid sequence encoding a CLAX (C-type Lectin, Activation Expressed) protein homologue, said CLAX protein homologue comprising the amino acid sequence as shown in SEQ ID NO:8.

8. The nucleic acid sequence of claim 7 comprising (a) the nucleic acid sequence as shown in SEQ ID NO:7; (b) the complement of (a); or (c) a nucleic acid sequence that differs from (a) or (b) due to degeneracy of the genetic code.

9. An expression vector comprising a nucleic acid sequence as claimed in any one of claims 1, 2, 3, 4, 5, 6, 7 or 8 and an expression control sequence operatively linked to the nucleic acid sequence.

10. A host cell including an expression vector comprising a nucleic acid sequence as claimed in any one of claims 1, 2, 3, 4, 5, 6, 7 or 8 and an expression control sequence operatively linked to the nucleic acid sequence.

11. A purified and isolated nucleic acid sequence encoding a CLAX (C-type Lectin, Activation Expressed) protein homologue comprising the cDNA clone contained in American Type Culture Collection (ATCC) Deposit Accession Number 203599.

12. A purified and isolated nucleic acid sequence encoding a CLAX (C-type Lectin, Activation Expressed) protein homologue comprising the cDNA clone contained in American Type Culture Collection (ATCC) Deposit Accession Number 203600.

13. A purified and isolated nucleic acid sequence encoding a CLAX (C-type Lectin, Activation Expressed) protein homologue comprising the cDNA clone contained in American Type Culture Collection (ATCC) Deposit Accession Number 203601.

* * * * *

SEQUENCE LISTING

<160> NUMBER OF SEQ ID NOS: 24

<210> SEQ ID NO 1
<211> LENGTH: 582
<212> TYPE: DNA
<213> ORGANISM: Homo sapiens

<400> SEQUENCE: 1

```
atgcatgaca gtaacaatgt ggagaaagac attacaccat ctgaattgcc tgcaaaccca      60
ggttgtctgc attcaaaaga gcattctatt aaagctacct taatttggcg cttattttc     120 ttaatcatgt ttctgacaat catagtgtgt ggaatggttg ctgctttaag cgcaataaga     180
gctaactgcc atcaagagcc atcagtatgt cttcaagctg catgcccaga aagctggatt     240
ggttttcaaa gaaagtgttt ctattttct gatgacacca agaactggac atcaagtcag     300
aggttttgtg actcacaaga tgctgatctt gctcaggttg aaagcttcca ggaactgaat     360
ttcctgttga gatataagg cccatctgat cactggattg ggctgagcag agaacaaggc     420
caaccatgga aatggataaa tggtactgaa tggacaagac agttagtcat gaaagaagat     480
ggtgccaact tgtatgttgc aaaggtttca caagttcctc gaatgaatcc aagacctgtc     540
```

```
atggtttcct atcctgggag caggagagtg tgcctatttg aa                         582
```

<210> SEQ ID NO 2
<211> LENGTH: 194
<212> TYPE: PRT
<213> ORGANISM: Homo sapiens

<400> SEQUENCE: 2

```
Met His Asp Ser Asn Asn Val Glu Lys Asp Ile Thr Pro Ser Glu Leu
1               5                   10                  15
Pro Ala Asn Pro Gly Cys Leu His Ser Lys Glu His Ser Ile Lys Ala
            20                  25                  30
Thr Leu Ile Trp Arg Leu Phe Phe Leu Ile Met Phe Leu Thr Ile Ile
        35                  40                  45
Val Cys Gly Met Val Ala Ala Leu Ser Ala Ile Arg Ala Asn Cys His
    50                  55                  60
Gln Glu Pro Ser Val Cys Leu Gln Ala Ala Cys Pro Glu Ser Trp Ile
65                  70                  75                  80
Gly Phe Gln Arg Lys Cys Phe Tyr Phe Ser Asp Thr Lys Asn Trp
                85                  90                  95
Thr Ser Ser Gln Arg Phe Cys Asp Ser Gln Asp Ala Asp Leu Ala Gln
            100                 105                 110
Val Glu Ser Phe Gln Glu Leu Asn Phe Leu Leu Arg Tyr Lys Gly Pro
        115                 120                 125
Ser Asp His Trp Ile Gly Leu Ser Arg Glu Gln Gly Gln Pro Trp Lys
    130                 135                 140
Trp Ile Asn Gly Thr Glu Trp Thr Arg Gln Leu Val Met Lys Glu Asp
145                 150                 155                 160
Gly Ala Asn Leu Tyr Val Ala Lys Val Ser Gln Val Pro Arg Met Asn
                165                 170                 175
Pro Arg Pro Val Met Val Ser Tyr Pro Gly Ser Arg Arg Val Cys Leu
            180                 185                 190
Phe Glu
```

<210> SEQ ID NO 3
<211> LENGTH: 519
<212> TYPE: DNA
<213> ORGANISM: Homo sapiens

<400> SEQUENCE: 3

```
tgtctgcatt caaaagagca ttctattaaa gctaccttaa tttggcgctt attttttctta    60
atcatgtttc tgacaatcat agtgtgtgga atggttgctg ctttaagcgc aataagagct   120
aactgccatc aagagccatc agtatgtctt caagctgcat gcccagaaag ctggattggt   180
tttcaaagaa agtgtttcta ttttctgat gacaccaaga actggacatc aagtcagagg   240
ttttgtgact cacaagatgc tgatcttgct caggttgaaa gcttccagga actgaatttc   300
ctgttgagat ataaaggccc atctgatcac tggattgggc tgagcagaga acaaggccaa   360
ccatggaaat ggataaatgg tactgaatgg acaagacagt tagtcatgaa agaagatggt   420
gccaacttgt atgttgcaaa ggtttcacaa gttcctcgaa tgaatccaag acctgtcatg   480
gtttcctatc ctgggagcag gagagtgtgc ctatttgaa                          519
```

<210> SEQ ID NO 4
<211> LENGTH: 173
<212> TYPE: PRT

<213> ORGANISM: Homo sapiens

<400> SEQUENCE: 4

Cys Leu His Ser Lys Glu His Ser Ile Lys Ala Thr Leu Ile Trp Arg
1               5                   10                  15

Leu Phe Phe Leu Ile Met Phe Leu Thr Ile Ile Val Cys Gly Met Val
            20                  25                  30

Ala Ala Leu Ser Ala Ile Arg Ala Asn Cys His Gln Glu Pro Ser Val
        35                  40                  45

Cys Leu Gln Ala Ala Cys Pro Glu Ser Trp Ile Gly Phe Gln Arg Lys
    50                  55                  60

Cys Phe Tyr Phe Ser Asp Asp Thr Lys Asn Trp Thr Ser Ser Gln Arg
65                  70                  75                  80

Phe Cys Asp Ser Gln Asp Ala Asp Leu Ala Gln Val Glu Ser Phe Gln
                85                  90                  95

Glu Leu Asn Phe Leu Leu Arg Tyr Lys Gly Pro Ser Asp His Trp Ile
            100                 105                 110

Gly Leu Ser Arg Glu Gln Gly Gln Pro Trp Lys Trp Ile Asn Gly Thr
        115                 120                 125

Glu Trp Thr Arg Gln Leu Val Met Lys Glu Asp Gly Ala Asn Leu Tyr
    130                 135                 140

Val Ala Lys Val Ser Gln Val Pro Arg Met Asn Pro Arg Pro Val Met
145                 150                 155                 160

Val Ser Tyr Pro Gly Ser Arg Arg Val Cys Leu Phe Glu
                165                 170

<210> SEQ ID NO 5
<211> LENGTH: 573
<212> TYPE: DNA
<213> ORGANISM: Homo sapiens

<400> SEQUENCE: 5
atgcatgaca gtaacaatgt ggagaaagac attacaccat ctgaattgcc tgcaaaccca      60
ggttgtctgc attcaaaaga gcattctatt aaagctacct taatttggcg cttattttc      120 ttaatcatgt ttctgacaat catagtgtgt ggaatggttg ctgctttaag cgcaataaga      180
gctaactgcc atcaagagcc atcagtatgt cttcaagctg catgcccaga aagctggatt      240
ggttttcaaa gaaagtgttt ctatttttct gatgacacca agaactggac atcaagtcag      300
aggttttgtg actcacaaga tgctgatctt gctcaggttg aaagcttcca ggaactgaat      360
ttcctgttga gatataaagg cccatctgat cactggattg gctgagcag agaacaaggc      420 caaccatgga aatggataaa tggtactgaa tggacaagac agtttcctat cctgggagca      480
ggagagtgtg cctatttgaa tgacaaaggt gccagtagtg ccaggcacta cacagagagg      540
aagtggattt gttccaaatc agatatacat gtc                                   573

<210> SEQ ID NO 6
<211> LENGTH: 191
<212> TYPE: PRT
<213> ORGANISM: Homo sapiens

<400> SEQUENCE: 6

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

```
Thr Leu Ile Trp Arg Leu Phe Phe Leu Ile Met Phe Leu Thr Ile Ile
             35                  40                  45

Val Cys Gly Met Val Ala Ala Leu Ser Ala Ile Arg Ala Asn Cys His
 50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                 85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190

<210> SEQ ID NO 7
<211> LENGTH: 318
<212> TYPE: DNA
<213> ORGANISM: Homo sapiens

<400> SEQUENCE: 7
gagcattcta ttaaagctac cttaatttgg cgcttatttt tcttaatcat gtttctgaca    60
atcatagtgt gtggaatggt tgctgcttta agcgcaataa gagctaactg ccatcaagag   120
ccatcagtat gtcttcaagc tgcatgccca gaaagctgga ttggttttca agaaagtgt    180 ttctattttt ctgatgacac caagaactgg acatcaagtc agaggttttg tgactcacaa   240
gatgctgatc ttgctcaggt tgaaagcttc caggaactgg tttcctatcc tgggagcagg   300
agagtgtgcc tatttgaa                                                  318

<210> SEQ ID NO 8
<211> LENGTH: 106
<212> TYPE: PRT
<213> ORGANISM: Homo sapiens

<400> SEQUENCE: 8

Glu His Ser Ile Lys Ala Thr Leu Ile Trp Arg Leu Phe Phe Leu Ile
1               5                  10                  15

Met Phe Leu Thr Ile Ile Val Cys Gly Met Val Ala Ala Leu Ser Ala
            20                  25                  30

Ile Arg Ala Asn Cys His Gln Glu Pro Ser Val Cys Leu Gln Ala Ala
        35                  40                  45

Cys Pro Glu Ser Trp Ile Gly Phe Gln Arg Lys Cys Phe Tyr Phe Ser
    50                  55                  60

Asp Asp Thr Lys Asn Trp Thr Ser Ser Gln Arg Phe Cys Asp Ser Gln
65                  70                  75                  80

Asp Ala Asp Leu Ala Gln Val Glu Ser Phe Gln Glu Leu Val Ser Tyr
                85                  90                  95

Pro Gly Ser Arg Arg Val Cys Leu Phe Glu
            100                 105
```

<210> SEQ ID NO 9
<211> LENGTH: 931
<212> TYPE: DNA
<213> ORGANISM: Homo sapiens

<400> SEQUENCE: 9

```
gcaaaatgca tgacagtaac aatgtggaga aagacattac accatctgaa ttgcctgcaa      60
acccaggttg tctgcattca aaagagcatt ctattaaagc taccttaatt tggcgcttat     120
ttttcttaat catgtttctg acaatcatag tgtgtggaat ggttgctgct ttaagcgcaa     180
taagagctaa ctgccatcaa gagccatcag tatgtcttca agctgcatgc ccagaaagct     240
ggattggttt tcaaagaaag tgtttctatt tttctgatga caccaagaac tggacatcaa     300
gtcagaggtt ttgtgactca aagatgctg atcttgctca ggttgaaagc ttccaggaac     360
tgaatttcct gttgagatat aaaggcccat ctgatcactg gattgggctg agcagagaac     420
aaggccaacc atggaaatgg ataaatggta ctgaatggac aagacagtta gtcatgaaag     480
aagatggtgc caacttgtat gttgcaaagg tttcacaagt tcctcgaatg aatccaagac     540
ctgtcatggt ttcctatcct gggagcagga gagtgtgcct atttgaatga caaaggtgcc     600
agtagtgcca ggcactacac agagaggaag tggatttgtt ccaaatcaga tatacatgtc     660
tagatgttac agcaaagccc caactaatct ttagaagcat attggaactg ataactccat     720
tttaaaatga cgaaagaatt tatttcttat accaacaggt atatgaaaat atgctcaata     780
tcactaataa ctgggaaaat acaatcaaaa tcatagtaaa atattacctg ttttcatggt     840
gctaatatta cctgttctcc cactgctaat gacatacccg agactgagta atttataaat     900
aaaagagatt taattgaaaa aaaaaaaaaa a                                    931
```

<210> SEQ ID NO 10
<211> LENGTH: 33
<212> TYPE: DNA
<213> ORGANISM: Homo sapiens

<400> SEQUENCE: 10

```
ctaggatcca agagctaact gccatcaaga gcc                                    33
```

<210> SEQ ID NO 11
<211> LENGTH: 33
<212> TYPE: DNA
<213> ORGANISM: Homo sapiens

<400> SEQUENCE: 11

```
cattctagat gcctggcact actggcacct ttg                                    33
```

<210> SEQ ID NO 12
<211> LENGTH: 331
<212> TYPE: PRT
<213> ORGANISM: Homo sapiens

<400> SEQUENCE: 12

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
    50                  55                  60
```

```
Trp Leu Phe Gln Asn Ser Ser Ser Lys Leu Pro Gln Pro Thr Phe Val
 65                  70                  75                  80

Tyr Met Ala Ser Ser His Asn Lys Ile Thr Trp Asp Glu Lys Leu Asn
                 85                  90                  95

Ser Ser Lys Leu Phe Ser Ala Met Arg Asp Thr Asn Asn Lys Tyr Val
            100                 105                 110

Leu Thr Leu Asn Lys Phe Ser Lys Glu Asn Glu Gly Tyr Tyr Phe Cys
        115                 120                 125

Ser Val Ile Ser Asn Ser Val Met Tyr Phe Ser Val Val Pro Val
    130                 135                 140

Leu Gln Lys Val Asn Ser Thr Thr Lys Pro Val Leu Arg Thr Pro
145                 150                 155                 160

Ser Pro Val His Pro Thr Gly Thr Ser Gln Pro Gln Arg Pro Glu Asp
                165                 170                 175

Cys Arg Pro Arg Gly Ser Val Lys Gly Thr Gly Leu Asp Phe Ala Cys
            180                 185                 190

Asp Pro Asp Pro Arg Ala Asn Cys His Gln Glu Pro Ser Val Cys Leu
            195                 200                 205

Gln Ala Ala Cys Pro Glu Ser Trp Ile Gly Phe Gln Arg Lys Cys Phe
        210                 215                 220

Tyr Phe Ser Asp Asp Thr Lys Asn Trp Thr Ser Ser Gln Arg Phe Cys
225                 230                 235                 240

Asp Ser Gln Asp Ala Asp Leu Ala Gln Val Glu Ser Phe Gln Glu Leu
                245                 250                 255

Asn Phe Leu Leu Arg Tyr Lys Gly Pro Ser Asp His Trp Ile Gly Leu
            260                 265                 270

Ser Arg Glu Gln Gly Gln Pro Trp Lys Trp Ile Asn Gly Thr Glu Trp
        275                 280                 285

Thr Arg Gln Leu Val Met Lys Glu Asp Gly Ala Asn Leu Tyr Val Ala
        290                 295                 300

Lys Val Ser Gln Val Pro Arg Met Asn Pro Arg Pro Val Met Val Ser
305                 310                 315                 320

Tyr Pro Gly Ser Arg Arg Val Cys Leu Phe Glu
                325                 330

<210> SEQ ID NO 13
<211> LENGTH: 328
<212> TYPE: PRT
<213> ORGANISM: Homo sapiens

<400> SEQUENCE: 13

Met Ala Ser Pro Leu Thr Arg Phe Leu Ser Leu Asn Leu Leu Leu
 1               5                  10                  15

Gly Glu Ser Ile Ile Leu Gly Ser Gly Glu Ala Lys Pro Gln Ala Pro
             20                  25                  30

Glu Leu Arg Ile Phe Pro Lys Lys Met Asp Ala Glu Leu Gly Gln Lys
         35                  40                  45

Val Asp Leu Val Cys Glu Val Leu Gly Ser Val Ser Gln Gly Cys Ser
     50                  55                  60

Trp Leu Phe Gln Asn Ser Ser Ser Lys Leu Pro Gln Pro Thr Phe Val
 65                  70                  75                  80

Tyr Met Ala Ser Ser His Asn Lys Ile Thr Trp Asp Glu Lys Leu Asn
                 85                  90                  95

Ser Ser Lys Leu Phe Ser Ala Met Arg Asp Thr Asn Asn Lys Tyr Val
```

-continued

```
                 100                 105                 110
Leu Thr Leu Asn Lys Phe Ser Lys Glu Asn Glu Gly Tyr Tyr Phe Cys
            115                 120                 125

Ser Val Ile Ser Asn Ser Val Met Tyr Phe Ser Val Val Pro Val
        130                 135                 140

Leu Gln Lys Val Asn Ser Thr Thr Lys Pro Val Leu Arg Thr Pro
145                 150                 155                 160

Ser Pro Val His Pro Thr Gly Thr Ser Gln Pro Gln Arg Pro Glu Asp
                165                 170                 175

Cys Arg Pro Arg Gly Ser Val Lys Gly Thr Gly Leu Asp Phe Ala Cys
            180                 185                 190

Asp Pro Asp Pro Arg Ala Asn Cys His Gln Glu Pro Ser Val Cys Leu
        195                 200                 205

Gln Ala Ala Cys Pro Glu Ser Trp Ile Gly Phe Gln Arg Lys Cys Phe
    210                 215                 220

Tyr Phe Ser Asp Asp Thr Lys Asn Trp Thr Ser Ser Gln Arg Phe Cys
225                 230                 235                 240

Asp Ser Gln Asp Ala Asp Leu Ala Gln Val Glu Ser Phe Gln Glu Leu
                245                 250                 255

Asn Phe Leu Leu Arg Tyr Lys Gly Pro Ser Asp His Trp Ile Gly Leu
            260                 265                 270

Ser Arg Glu Gln Gly Gln Pro Trp Lys Trp Ile Asn Gly Thr Glu Trp
        275                 280                 285

Thr Arg Gln Phe Pro Ile Leu Gly Ala Gly Glu Cys Ala Tyr Leu Asn
    290                 295                 300

Asp Lys Gly Ala Ser Ser Ala Arg His Tyr Thr Glu Arg Lys Trp Ile
305                 310                 315                 320

Cys Ser Lys Ser Asp Ile His Val
                325
```

<210> SEQ ID NO 14
<211> LENGTH: 269
<212> TYPE: PRT
<213> ORGANISM: Homo sapiens

<400> SEQUENCE: 14

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
    50                  55                  60

Trp Leu Phe Gln Asn Ser Ser Ser Lys Leu Pro Gln Pro Thr Phe Val
65                  70                  75                  80

Tyr Met Ala Ser Ser His Asn Lys Ile Thr Trp Asp Glu Lys Leu Asn
                85                  90                  95

Ser Ser Lys Leu Phe Ser Ala Met Arg Asp Thr Asn Asn Lys Tyr Val
            100                 105                 110

Leu Thr Leu Asn Lys Phe Ser Lys Glu Asn Glu Gly Tyr Tyr Phe Cys
        115                 120                 125

Ser Val Ile Ser Asn Ser Val Met Tyr Phe Ser Val Val Pro Val
    130                 135                 140
```

```
Leu Gln Lys Val Asn Ser Thr Thr Lys Pro Val Leu Arg Thr Pro
145                 150                 155                 160

Ser Pro Val His Pro Thr Gly Thr Ser Gln Pro Gln Arg Pro Glu Asp
                165                 170                 175

Cys Arg Pro Arg Gly Ser Val Lys Gly Thr Gly Leu Asp Phe Ala Cys
            180                 185                 190

Asp Pro Asp Pro Arg Ala Asn Cys His Gln Glu Pro Ser Val Cys Leu
        195                 200                 205

Gln Ala Ala Cys Pro Glu Ser Trp Ile Gly Phe Gln Arg Lys Cys Phe
    210                 215                 220

Tyr Phe Ser Asp Asp Thr Lys Asn Trp Thr Ser Ser Gln Arg Phe Cys
225                 230                 235                 240

Asp Ser Gln Asp Ala Asp Leu Ala Gln Val Glu Ser Phe Gln Glu Leu
                245                 250                 255

Val Ser Tyr Pro Gly Ser Arg Arg Val Cys Leu Phe Glu
            260                 265

<210> SEQ ID NO 15
<211> LENGTH: 78
<212> TYPE: PRT
<213> ORGANISM: Homo sapiens

<400> SEQUENCE: 15

Ala Ala Cys Pro Glu Ser Trp Ile Gly Phe Gln Arg Lys Cys Phe Tyr
1               5                   10                  15

Phe Ser Asp Asp Thr Lys Asn Trp Thr Ser Ser Gln Arg Phe Cys Asp
                20                  25                  30

Ser Gln Asp Ala Asp Leu Ala Gln Val Glu Ser Phe Gln Glu Leu Asn
            35                  40                  45

Phe Leu Leu Arg Tyr Lys Gly Pro Ser Asp His Trp Ile Gly Leu Ser
        50                  55                  60

Arg Glu Gln Gly Gln Pro Trp Lys Trp Ile Asn Gly Thr Glu
65                  70                  75

<210> SEQ ID NO 16
<211> LENGTH: 78
<212> TYPE: PRT
<213> ORGANISM: Homo sapiens

<400> SEQUENCE: 16

Ala Ala Cys Pro Glu Ser Trp Ile Gly Phe Gln Arg Lys Cys Phe Tyr
1               5                   10                  15

Phe Ser Asp Asp Thr Lys Asn Trp Thr Ser Ser Gln Arg Phe Cys Asp
                20                  25                  30

Ser Gln Asp Ala Asp Leu Ala Gln Val Glu Ser Phe Gln Glu Leu Asn
            35                  40                  45

Phe Leu Leu Arg Tyr Lys Gly Pro Ser Asp His Trp Ile Gly Leu Ser
        50                  55                  60

Arg Glu Gln Gly Gln Pro Trp Lys Trp Ile Asn Gly Thr Glu
65                  70                  75

<210> SEQ ID NO 17
<211> LENGTH: 47
<212> TYPE: PRT
<213> ORGANISM: Homo sapiens

<400> SEQUENCE: 17

Ala Ala Cys Pro Glu Ser Trp Ile Gly Phe Gln Arg Lys Cys Phe Tyr
```

```
                    1               5                    10                   15
Phe Ser Asp Asp Thr Lys Asn Trp Thr Ser Ser Gln Arg Phe Cys Asp
                    20                  25                  30

Ser Gln Asp Ala Asp Leu Ala Gln Val Glu Ser Phe Gln Glu Leu
                    35                  40                  45

<210> SEQ ID NO 18
<211> LENGTH: 78
<212> TYPE: PRT
<213> ORGANISM: Homo sapiens

<400> SEQUENCE: 18

Ser Ser Cys Ser Glu Asp Trp Val Gly Tyr Gln Arg Lys Cys Tyr Phe
1               5                   10                  15

Ile Ser Thr Val Lys Arg Ser Trp Thr Ser Ala Gln Asn Ala Cys Ser
                    20                  25                  30

Glu His Gly Ala Thr Leu Ala Val Ile Asp Ser Glu Lys Asp Met Asn
                    35                  40                  45

Phe Leu Lys Arg Tyr Ala Gly Arg Glu Glu His Trp Val Gly Leu Lys
            50                  55                  60

Lys Glu Pro Gly His Pro Trp Lys Trp Ser Asn Gly Lys Glu
65                  70                  75

<210> SEQ ID NO 19
<211> LENGTH: 79
<212> TYPE: PRT
<213> ORGANISM: Homo sapiens

<400> SEQUENCE: 19

His Val Cys Pro Asn Ala Trp Val Gly Phe Gln Gly Lys Cys Tyr Tyr
1               5                   10                  15

Phe Ser Asp Thr Glu Ser Asp Trp Asn Ser Ser Arg Glu His Cys His
                    20                  25                  30

Arg Leu Gly Ala Ser Leu Ala Thr Leu Asp Thr Lys Glu Glu Met Glu
                    35                  40                  45

Phe Met Leu Gln Tyr Gln Arg Pro Ala Asp Arg Trp Ile Gly Leu His
            50                  55                  60

Arg Ala Glu Gly Asp Glu His Trp Thr Trp Ala Asp Gly Ser Ala
65                  70                  75

<210> SEQ ID NO 20
<211> LENGTH: 78
<212> TYPE: PRT
<213> ORGANISM: Homo sapiens

<400> SEQUENCE: 20

Ser Leu Cys Pro Tyr Asp Trp Ile Gly Phe Gln Asn Lys Cys Tyr Tyr
1               5                   10                  15

Phe Ser Lys Glu Glu Gly Asp Trp Asn Ser Ser Lys Tyr Asn Cys Ser
                    20                  25                  30

Thr Gln His Ala Asp Leu Thr Ile Ile Asp Asn Ile Glu Met Asn
                    35                  40                  45

Phe Leu Arg Arg Tyr Lys Cys Ser Ser Asp His Trp Ile Gly Leu Lys
            50                  55                  60

Met Ala Lys Asn Arg Thr Gly Gln Trp Val His Gly Ala Thr
65                  70                  75

<210> SEQ ID NO 21
```

```
<211> LENGTH: 77
<212> TYPE: PRT
<213> ORGANISM: Homo sapiens

<400> SEQUENCE: 21

Thr Cys Cys Pro Val Asn Trp Val Glu His Gln Gly Ser Cys Tyr Trp
1               5                   10                  15

Phe Ser His Ser Gly Lys Ala Trp Ala Glu Ala Glu Lys Tyr Cys Gln
            20                  25                  30

Leu Glu Asn Ala His Leu Val Val Ile Asn Ser Trp Glu Glu Gln Lys
        35                  40                  45

Phe Ile Val Gln His Thr Asn Pro Phe Asn Trp Ile Gly Leu Thr
    50                  55                  60

Asp Ser Asp Gly Ser Trp Lys Trp Val Asp Gly Thr Asp
65                  70                  75

<210> SEQ ID NO 22
<211> LENGTH: 77
<212> TYPE: PRT
<213> ORGANISM: Homo sapiens

<400> SEQUENCE: 22

Cys Ser Cys Gln Glu Lys Trp Val Gly Tyr Arg Cys Asn Cys Tyr Phe
1               5                   10                  15

Ile Ser Ser Glu Gln Lys Thr Trp Asn Glu Ser Arg His Leu Cys Ala
            20                  25                  30

Ser Gln Lys Ser Ser Leu Leu Gln Leu Gln Asn Thr Asp Glu Leu Asp
        35                  40                  45

Phe Met Ser Ser Gln Gln Phe Tyr Trp Ile Gly Leu Ser Tyr Ser
    50                  55                  60

Glu Glu His Thr Ala Trp Leu Trp Glu Asn Gly Ser Ala
65                  70                  75

<210> SEQ ID NO 23
<211> LENGTH: 76
<212> TYPE: PRT
<213> ORGANISM: Homo sapiens

<400> SEQUENCE: 23

Pro Ser Cys Pro Asp Arg Trp Met Lys Tyr Gly Asn His Cys Tyr Tyr
1               5                   10                  15

Phe Ser Val Glu Glu Lys Asp Trp Asn Ser Ser Leu Glu Phe Cys Leu
            20                  25                  30

Ala Arg Asp Ser His Leu Leu Val Ile Thr Asp Asn Gln Glu Met Ser
        35                  40                  45

Leu Leu Gln Val Phe Leu Ser Glu Ala Phe Cys Trp Ile Gly Leu Arg
    50                  55                  60

Asn Met Ser Gly Trp Arg Trp Glu Asp Gly Ser Pro
65                  70                  75

<210> SEQ ID NO 24
<211> LENGTH: 79
<212> TYPE: PRT
<213> ORGANISM: Homo sapiens

<400> SEQUENCE: 24

Asn Thr Cys Pro Glu Lys Trp Ile Asn Phe Gln Arg Lys Cys Tyr Tyr
1               5                   10                  15

Phe Gly Lys Gly Thr Lys Gln Trp Val His Ala Arg Tyr Ala Cys Asp
```

-continued

```
                    20                  25                  30
Asp Met Glu Gly Gln Leu Val Ser Ile His Ser Pro Glu Glu Gln Asp
        35                  40                  45
Phe Leu Thr Lys His Ala Ser His Thr Gly Ser Trp Ile Gly Leu Arg
    50                  55                  60
Asn Leu Asp Leu Lys Gly Glu Phe Ile Trp Val Asp Gly Ser His
65                  70                  75
```